United States Patent
Borek et al.

(10) Patent No.: US 11,419,624 B2
(45) Date of Patent: Aug. 23, 2022

(54) DEVICES, SYSTEMS AND METHODS FOR TISSUE RESECTION

(71) Applicant: Boston Scientific Scimed, Inc., Maple Grove, MN (US)

(72) Inventors: Michael M. Borek, Holden, MA (US); Micah Flock, Somerville, MA (US); Julianne Grainger, Boston, MA (US); Christopher A. Olmeda, Maynard, MA (US); Katie Olmeda, Maynard, MA (US); Rachel M. Williams, Framingham, MA (US); Morgan Zhu, Somerville, MA (US); John B. Golden, Norton, MA (US); Chris Jicka, Upper Saddle River, NJ (US); Austin G. Johnson, Hudson, MA (US); Caleb A. Valdes, Lowell, MA (US); Serena Scott, Worcester, MA (US); Michael K. Ford, Waltham, MA (US); Kyle P. Moore, Milton, GA (US); Janice Courtois, Clinton, MA (US); Prashanth Somasundaram, Boston, MA (US); Ryan V. Wales, Northborough, MA (US); Scott E. Brechbiel, Acton, MA (US); Rachael Campion, Boston, MA (US); Tara A. Jarobski, North Oxford, MA (US); Danny S. Lee, Cambridge, MA (US); Alexander J. Burnham, Southbury, CT (US); Christopher K. Oto, Boston, MA (US); Nicholas J. Mazzola, Hudson, MA (US); Kevin L. Bagley, Dedham, MA (US); Shaun D. Comee, Fiskdale, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 373 days.

(21) Appl. No.: 16/419,926

(22) Filed: May 22, 2019

(65) Prior Publication Data
US 2019/0357934 A1 Nov. 28, 2019

Related U.S. Application Data

(60) Provisional application No. 62/675,681, filed on May 23, 2018.

(51) Int. Cl.
*A61B 17/32* (2006.01)
*A61B 1/313* (2006.01)
(Continued)

(52) U.S. Cl.
CPC ...... *A61B 17/320016* (2013.01); *A61B 1/313* (2013.01); *A61B 17/115* (2013.01);
(Continued)

(58) Field of Classification Search
CPC ............... A61B 17/1114; A61B 17/115; A61B 17/1155; A61B 17/12136;
(Continued)

(56) References Cited

U.S. PATENT DOCUMENTS 5,395,030 A    3/1995  Kuramoto et al.
7,141,055 B2  11/2006  Abrams et al.
(Continued)

FOREIGN PATENT DOCUMENTS

CA     2988249 A1   12/2016
JP     H06-47050 A   2/1994
(Continued)

OTHER PUBLICATIONS

International Search Report and Written Opinion for International application No. PCT/US2019/033590, dated Nov. 13, 2019, 12 pages.

*Primary Examiner* — Mohamed G Gabr
(74) *Attorney, Agent, or Firm* — Seager, Tufte & Wickhem, LLP

(57) ABSTRACT

Exemplary embodiments of the present disclosure relate to devices, systems, and methods for tissue resection in a body lumen of a patient, and may include a body extending along an axis and a distal cap positioned distally of the body and coupled to a shaft extending along the axis. The body and the distal cap may be movable relative to each other. An anchoring mechanism may be capable of engaging the body and the distal cap proximate a selected tissue for resection in the body lumen. A tissue capture device may be deployable from the tissue resection device such that a selected tissue for resection is securable by the tissue capture device. The tissue resection device may further include a tissue resecting device for resecting the selected tissue for resection.

15 Claims, 17 Drawing Sheets

(51) Int. Cl.
*A61B 17/115* (2006.01)
*A61B 17/12* (2006.01)
*A61B 17/00* (2006.01)

(52) U.S. Cl.
CPC ............ *A61B 17/12136* (2013.01); *A61B 2017/00269* (2013.01); *A61B 2017/12127* (2013.01)

(58) Field of Classification Search
CPC ............ A61B 17/320016; A61B 1/313; A61B 2017/00269; A61B 2017/00818; A61B 2017/0419; A61B 2017/0647; A61B 2017/1132; A61B 2017/12127; A61B 2017/306; A61B 90/361; A61B 90/37
See application file for complete search history.

(56) References Cited

U.S. PATENT DOCUMENTS

| | | | |
|---|---|---|---|
| 7,338,505 B2 | 3/2008 | Belson | |
| 8,529,591 B2 | 9/2013 | Nakamura et al. | |
| 8,590,764 B2 | 11/2013 | Hartwick et al. | |
| 8,911,458 B2 | 12/2014 | Bassan et al. | |
| 9,155,539 B2 | 10/2015 | Gronberg et al. | |
| 9,295,470 B2 | 3/2016 | Baur et al. | |
| 9,743,931 B2 | 8/2017 | Gronberg | |
| 9,820,746 B2 | 11/2017 | Imran | |
| 10,130,502 B2 | 11/2018 | Chamorro et al. | |
| 10,307,280 B2 | 6/2019 | Zeiner et al. | |
| 10,420,665 B2 | 9/2019 | Sharma et al. | |
| 10,548,753 B2 | 2/2020 | Rousseau | |
| 2002/0020732 A1* | 2/2002 | Adams | A61B 17/072 227/180.1 |
| 2003/0018236 A1 | 1/2003 | Adams | |
| 2006/0111704 A1 | 5/2006 | Brenneman et al. | |
| 2010/0213239 A1 | 8/2010 | Rebuffat et al. | |
| 2011/0306994 A1* | 12/2011 | Bassan | A61B 17/0469 606/153 |
| 2012/0108897 A1 | 5/2012 | Adams | |
| 2017/0281181 A1 | 10/2017 | Matonick et al. | |
| 2017/0348016 A1 | 12/2017 | Motai et al. | |

FOREIGN PATENT DOCUMENTS

| | | |
|---|---|---|
| JP | 2011-224031 A | 11/2011 |
| WO | 2017168593 A1 | 10/2017 |

* cited by examiner

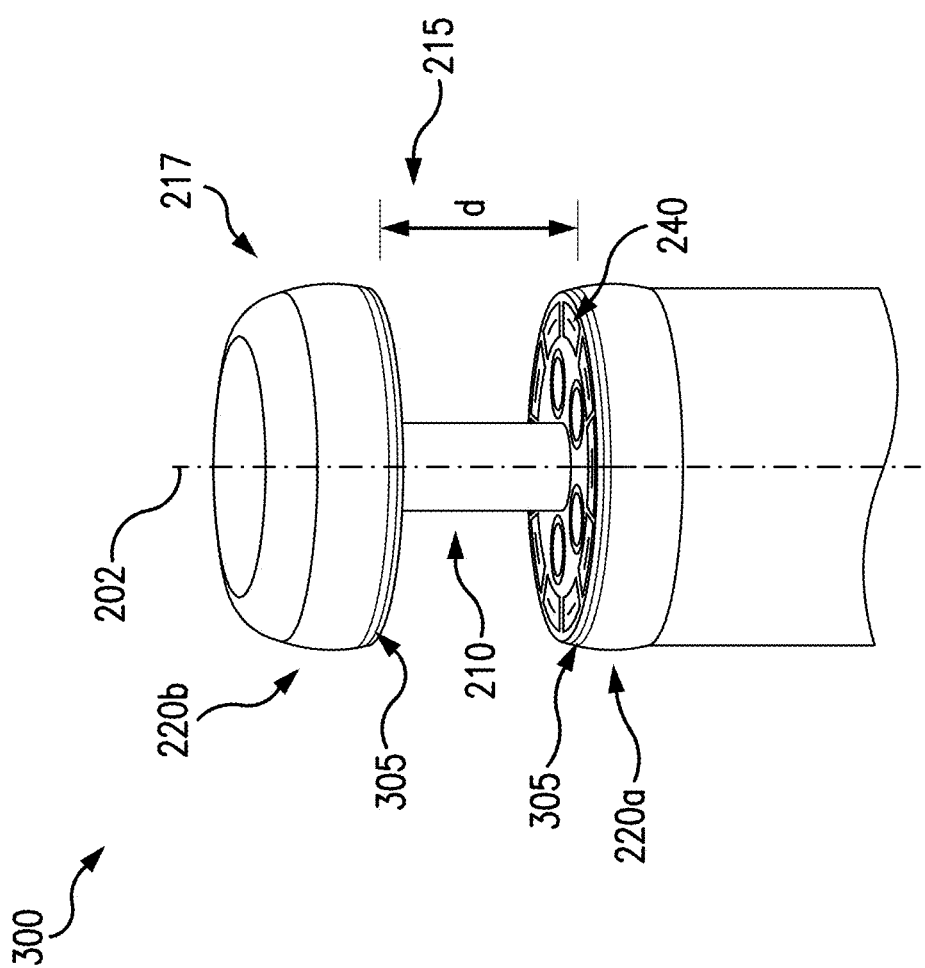

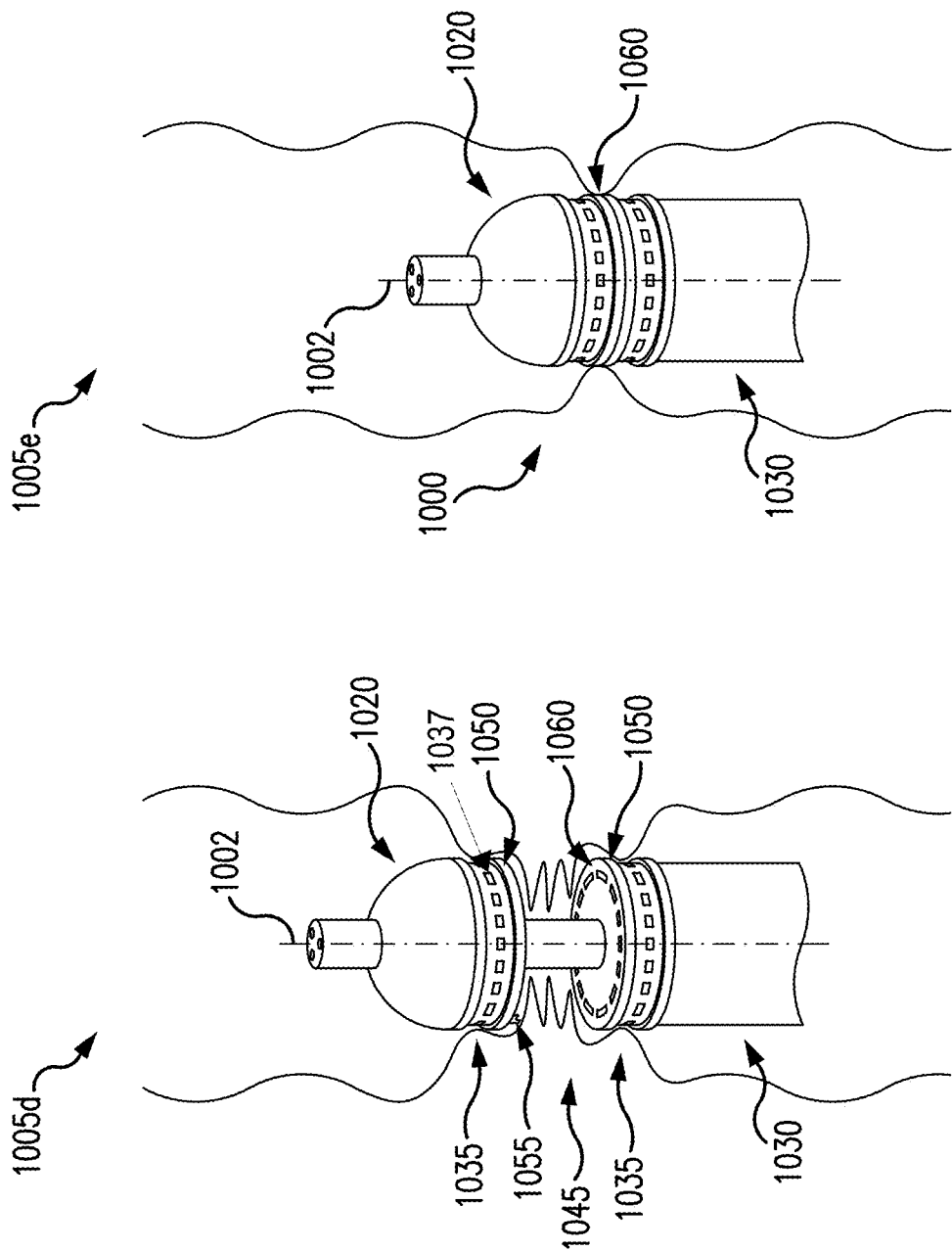

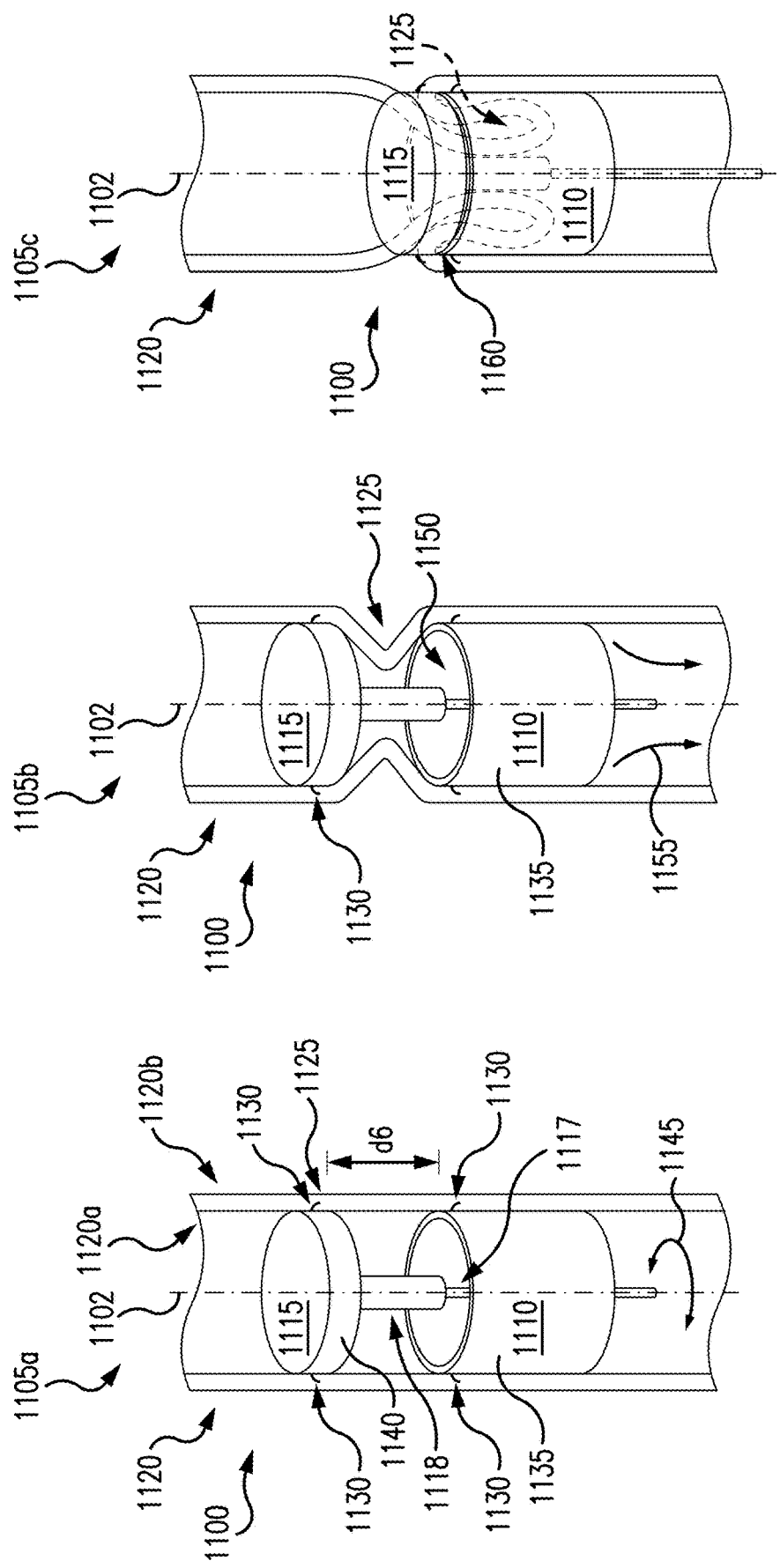

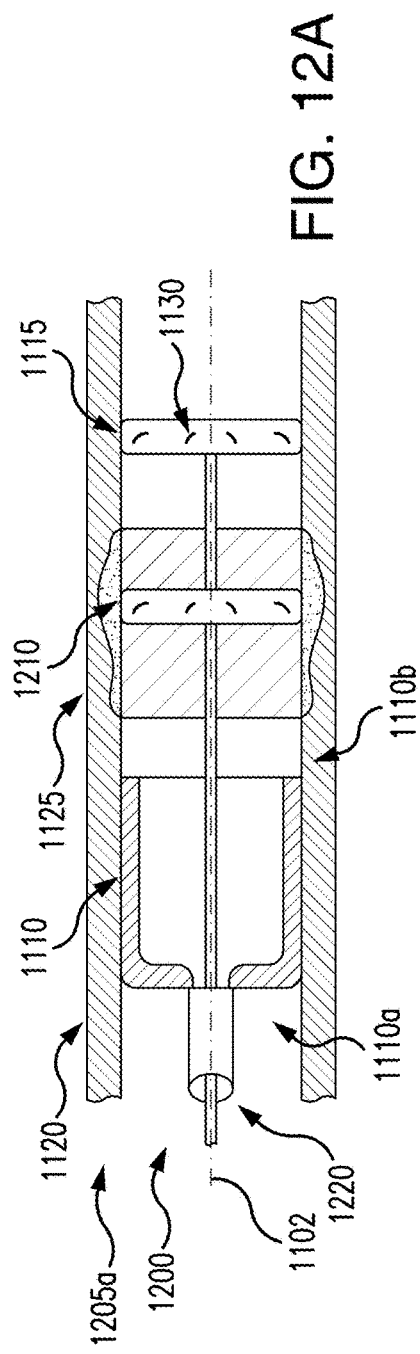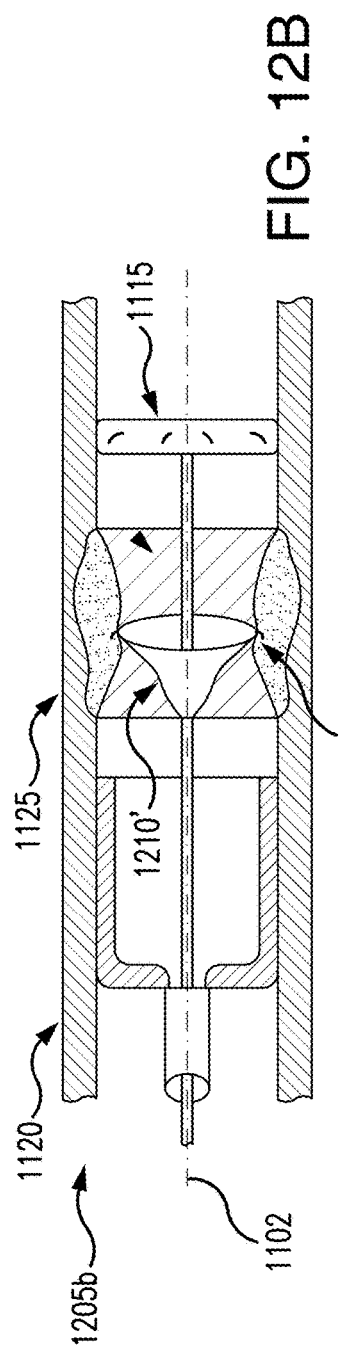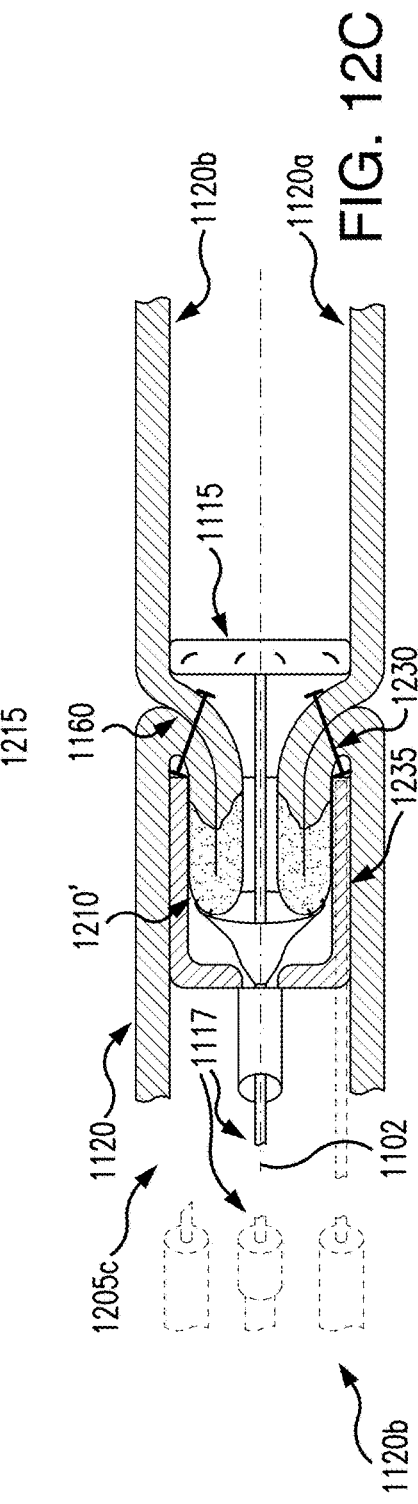

DEVICES, SYSTEMS AND METHODS FOR TISSUE RESECTION

CROSS REFERENCE TO RELATED APPLICATIONS

This application claims the benefit of priority under 35 U.S.C. § 119 to U.S. Provisional Patent Application Ser. No. 62/675,681, filed on May 23, 2018, which is incorporated by reference in its entirety for all purposes.

FIELD

The present disclosure relates generally to devices, systems, and methods for performing endoscopic procedures, and, more particularly, tissue resection devices for endoscopic mucosal resection (EMR) and/or endoscopic submucosal dissection (ESD) procedures, including such devices, system and methods to achieve partially or fully circumferential endoscopic full thickness resection (eFTR), tissue closure and/or tissue apposition.

BACKGROUND

Endoscopic mucosal resection (EMR) and/or endoscopic submucosal dissection (ESD) procedures may be used to resect benign or diseased tissue, e.g., lesions, cancerous tumors, and/or other anomalies, from a patient's gastrointestinal system. In some patients, full thickness resection (FTR), which may be partially or fully circumferential in a body lumen, may be necessary to ensure complete removal of the diseased tissue, as opposed to removal of only mucosal layers of the gastrointestinal system.

However, FTR procedures may pose additional challenges such as anatomical difficulties of removing tissue adjacent critical internal organs and other sensitive structures, as well as risk of post-operative leakage, potentially increasing a patient's health risk in undergoing an FTR procedure.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a device for tissue resection in a body lumen may include a body extending along an axis, and a distal cap positioned distally of the body and coupled to a shaft extending along the axis. The body and the distal cap may be movable relative to each other. The device for tissue resection may further include an anchoring mechanism capable of engaging the body and the distal cap proximate a selected tissue for resection in the body lumen. The device for tissue resection may further include a tissue capture device deployable from the tissue resection device, and the selected tissue for resection may be securable by the tissue capture device. The device for tissue resection may further include a tissue resecting device for resecting the selected tissue for resection.

In various of the foregoing and other embodiments of the present disclosure, the tissue resection device may further include a tissue closure device. The anchoring mechanism may include a first balloon disposed on the distal cap and a second balloon disposed on the body. The first and second balloons may be expandable to engage the body lumen such that the selected tissue for resection is between the first and second balloons. The tissue capture device may include one or more posts disposed circumferentially around a surface of the body and extendable from the body in a direction along the axis for securing the selected tissue for resection against the distal cap. the tissue closure device may include a closure mechanism for joining portions of the body lumen. The tissue resecting device may include a blade disposed circumferentially around a surface of the body and extendable from the body in a direction along the axis for resecting the selected tissue for resection. The tissue resecting device may include a blade disposed circumferentially around a surface of the distal cap and extendable from the distal cap in a direction along the axis for resecting the selected tissue for resection. The tissue resecting device may be disposed on an outer shaft and the distal cap may be disposed on an inner shaft. The tissue resecting device may be extendable from the distal cap in response to the inner shaft being movable relative to the outer shaft.

According to an exemplary embodiment of the present disclosure, a system for tissue resection in a body lumen may include a tissue resection device. The tissue resection device may include a body extending along an axis, and a distal cap positioned distally of the body and coupled to a shaft extending along the axis. The body and the distal cap may be movable relative to each other. The tissue resection device may include an anchoring mechanism capable of engaging the body and the distal cap proximate a selected tissue for resection in the body lumen. The system may further include a visualization device for visualizing positioning of the tissue resection device in the body lumen relative to the selected tissue for resection.

In various of the foregoing and other embodiments of the present disclosure, the system may further include a tissue capture device deployable from the tissue resection device such that the selected tissue for resection is securable by the tissue capture device. The system may further include a tissue resecting device for resecting the selected tissue for resection, and a tissue closure device. The anchoring mechanism may include a first balloon disposed on the distal cap and a second balloon disposed on the body. The first and second balloons may be expandable to engage the body lumen such that the selected tissue for resection may be between the first and second balloons. The tissue capture device may include one or more posts disposed circumferentially around a surface of the body and extendable from the body in a direction along the axis for securing the selected tissue for resection against the distal cap. The tissue resecting device may include a blade disposed circumferentially around a surface of the body and extendable from the body in a direction along the axis for resecting the selected tissue for resection. The tissue resecting device may include a blade disposed circumferentially around a surface of the distal cap and extendable from the distal cap in a direction along the axis for resecting the selected tissue for resection. The tissue resecting device may be disposed on an outer shaft and the distal cap is disposed on an inner shaft. The tissue resecting device may be extendable from the distal cap in response to the inner shaft being movable relative to the outer shaft.

According to an exemplary embodiment of the present disclosure, a method for resecting tissue in a body lumen may include delivering a tissue resection device to a position of a selected tissue for resection in the body lumen. The tissue resection device may include a body extending along an axis. The tissue resection device may further include a distal cap positioned distally of the body and coupled to a shaft extending along the axis. The body and the distal cap may be movable relative to each other. The tissue resection device may further include an anchoring mechanism for engaging the body and the distal cap proximate the selected tissue for resection. The anchoring mechanism may include a first balloon disposed on the distal cap and a second balloon disposed on the body. The method may further include expanding the first balloon to engage the distal cap to the body lumen, extending the distal cap and the body a distance apart from each other along the axis, and expanding the second balloon to engage the body to the body lumen.

In various of the foregoing and other embodiments of the present disclosure, the method may further include closing the distal cap and the body to pleat the selected tissue for resection between the first and second balloon. The method may further include moving the pleated selected tissue for resection inward towards the axis of the tissue resection device. The method may further include securing the pleated selected tissue for resection by a tissue capture device, wherein the securing includes extending one or more posts disposed circumferentially around a surface of the body in a direction along the axis. The method may further include joining portions of the body lumen by a tissue closure device, wherein the tissue closure device includes a closure mechanism. The method may further include resecting the selected tissue for resection by a tissue resecting device. The tissue resecting device may include a blade disposed circumferentially around a surface of the body, and the resecting may include extending the blade from the body in a direction along the axis. The tissue resecting device may further include a blade disposed circumferentially around a surface of the distal cap. The resecting may include extending the blade from the distal cap in a direction along the axis.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 3 illustrates an exemplary embodiment of a tissue resection device in accordance with the present disclosure;

FIGS. 10A-10E illustrate an exemplary process for resecting tissue using a tissue resection device in accordance with the present disclosure.

FIGS. 11A-11C illustrate an exemplary tissue resection device and process for resecting tissue in accordance with the present disclosure;

FIGS. 12A-12C illustrate an exemplary tissue resection device and process for resecting tissue in accordance with the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

It may be understood that references to "proximal" may be defined as an end of the systems and devices closest to the entry point of the patient and "distal" may be defined as an end of the systems and devices closest to the desired location of the system and devices in the patient (e.g., a patient's gastrointestinal system).

Figure 1:
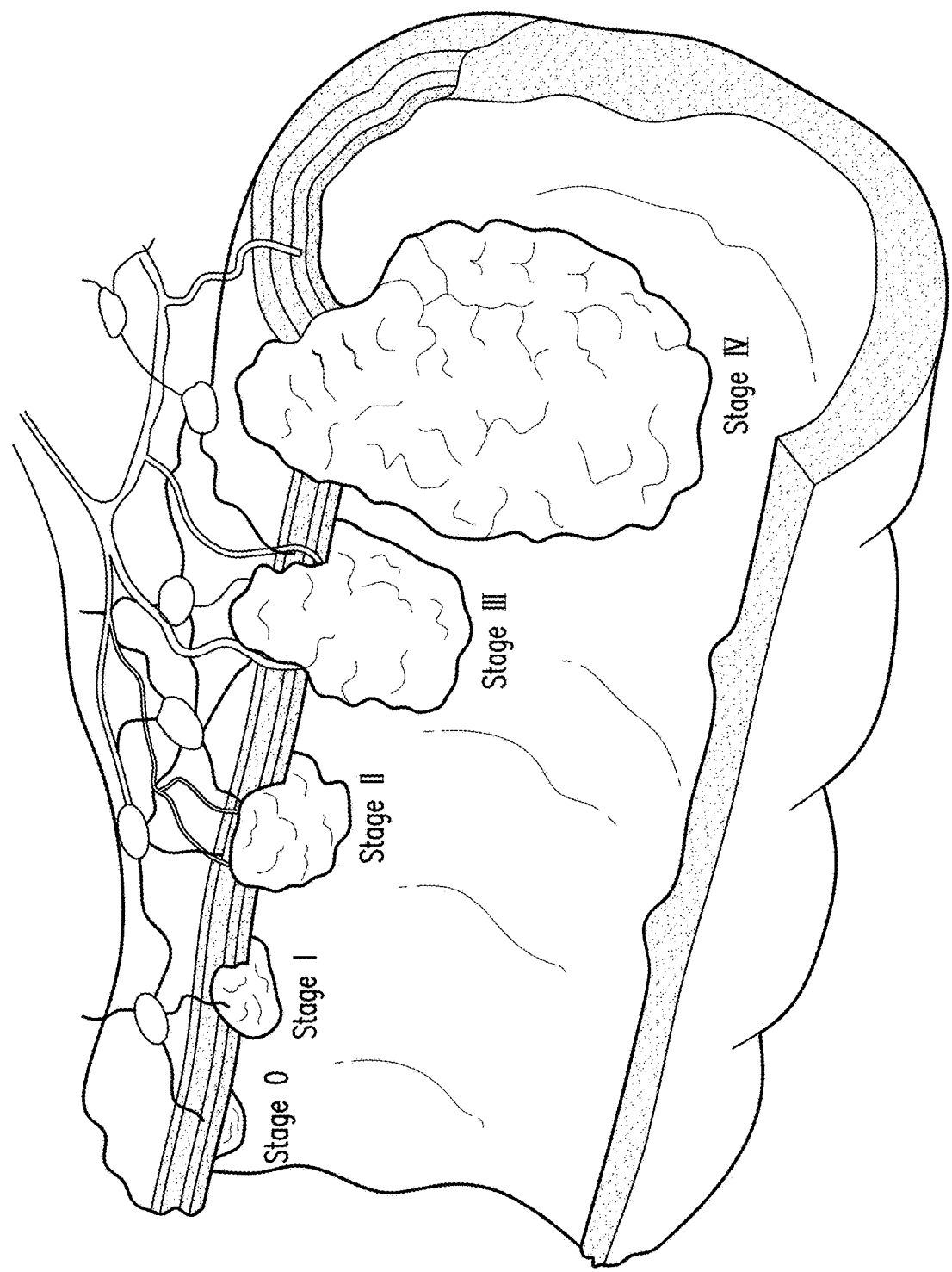
FIG. 1 illustrates a body lumen of a patient.

As described above, patients with diseased or other tissue in the gastrointestinal system may require resection. Referring to FIG. 1, various sized lesions are illustrated in a body lumen (e.g., gastrointestinal system) of a patient. As shown, earlier stages of diseased tissue may not extend through all the layers of the body lumen, which may allow for resection of only the affected tissue layers. However, as diseased tissue advances to later stages, resection of the entire tissue portion (e.g., full thickness resection) may be needed to fully excise the diseased tissue from the patient. Exemplary embodiments of devices, systems, and methods for partial or full thickness tissue resection in accordance with the present disclosure may allow for a selected tissue section containing diseased tissue to be contained and resected from surrounding tissue, the surrounding tissue then being joined together to close a gap formed by the resection of the selected tissue. In some embodiments, the tissue resection may be fully circumferential, e.g., extending 360° around a body lumen. In other embodiments, the tissue resection may be partially circumferential, e.g., extending less than 360° around a body lumen. Although "resection" is used throughout the disclosure, exemplary embodiments of the present disclosure may encompass resecting, dissecting, removing, ablating, cutting vaporizing, freezing, etc., and may be full thickness, partial thickness, and in instances of a procedure occurring in a body lumen, may be partial and/or fully circumferential.

Figure 2:
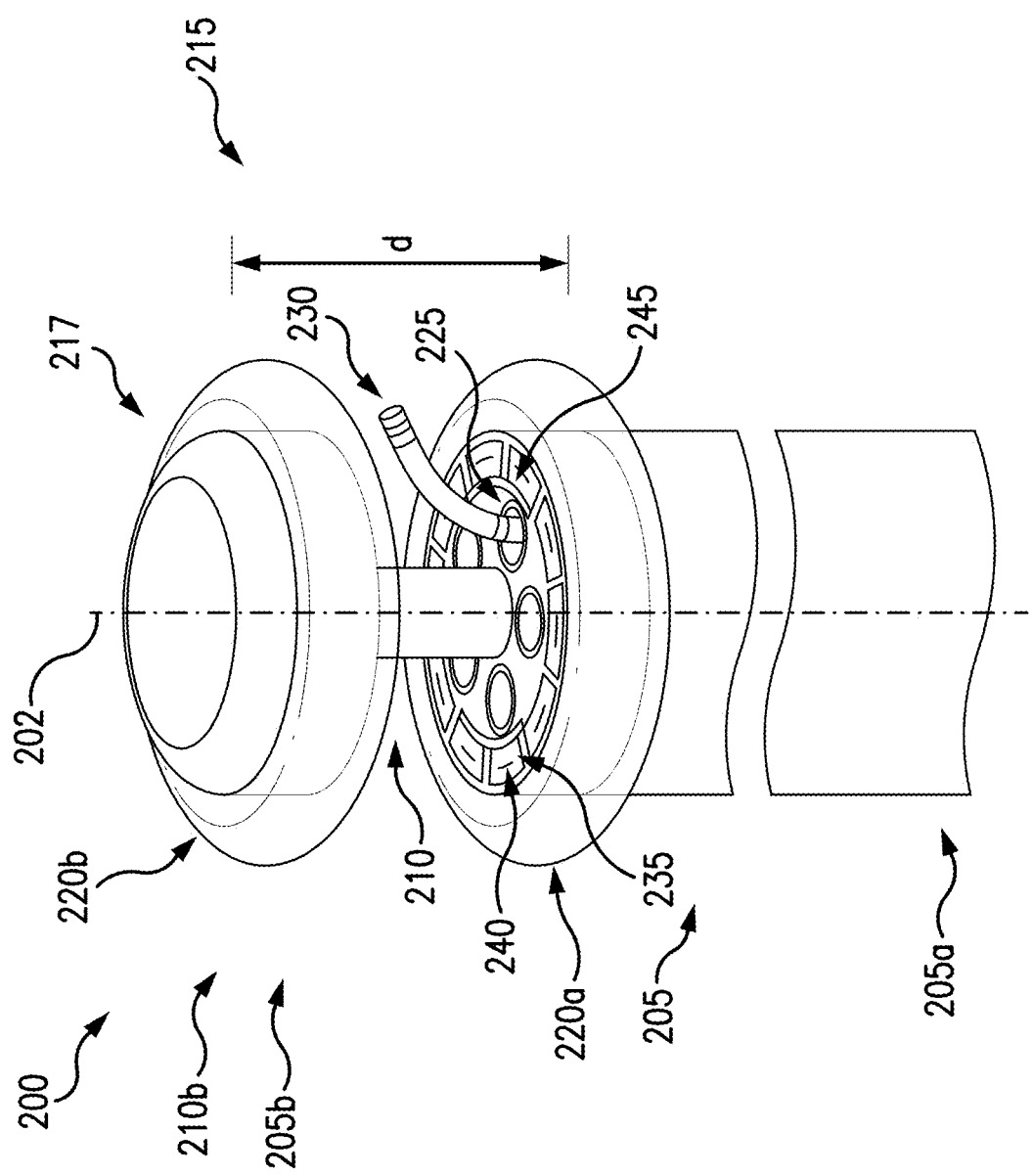
FIG. 2 illustrates an exemplary embodiment of a tissue resection device in accordance with the present disclosure.

Referring now to FIG. 2, an exemplary embodiment of a resection device 200, e.g., an endoluminal resection device, in accordance with the present disclosure is shown. The device 200 may be delivered to a site in a patient for resecting a selected portion of tissue. In some embodiments, the selected tissue may be in a body lumen such as an intestine, colon, and/or other gastrointestinal system. The resection device 200 may be configured for full thickness resection of a large intestine, although it is envisioned that the resection device 200 may be configured for other anatomical resecting as well. The device 200 may include a body 205 extending along an axis 202 and having a proximal end 205a and a distal end 205b. In some embodiments, the body 205 may be a lumen, or hollow tube. A handle (not shown) may be coupled to the proximal end 205a for actuation of the distal end 205b by a medical professional. Although the body lumen is described with respect to the gastrointestinal system, including but not limited to an intestine, colon, duodenum, and/or other gastrointestinal system, it is understood that exemplary embodiments of devices, systems, and methods of the present disclosure may apply to any body lumen in a patient.

The body 205 may include a shaft 210, extending coaxial to the body 205 along the axis 202. In embodiments, the shaft 210 may be movable relative to the body 205 along the axis 202. An anchoring mechanism 215 may be coupled to the body 205, e.g., to anchor the device 200 to an inner surface of the body lumen. In embodiments, a portion of the anchoring mechanism 215 may be coupled to a distal end 210b of the shaft 210 as a distal cap 217, extending distal of the distal end 205b of the body 205. For example, as the shaft 210 moves along the axis 202, a portion of the anchoring mechanism 215 coupled to the shaft 210, e.g., on the distal cap 217, may be movable relative to another portion of the anchoring mechanism 215, e.g., coupled to the body 205.

In some embodiments, the anchoring mechanism 215 may be one or more expandable balloons 220a, 220b, . . . 220n. Although a first balloon 220a and a second balloon 220b are illustrated in FIG. 2, it may be understood that any number "n" of balloons may be utilized in the anchoring mechanism. A first balloon 220a may be disposed on a proximal portion of the distal end 205b of the body 205, e.g., coupled to the body 205. A second balloon 220b may be disposed on a distal portion of the distal end 205b, e.g., coupled to the shaft 210 on the distal cap 217, and distal of the first balloon 220a. The first and second balloons 220a, 220b may be positionable along the axis 202, e.g., by the body 205 and/or the shaft 210. For example, the shaft 210 may extend the distal cap 217 and second balloon 220b apart from the first balloon 220a on the body 205.

Figure 5C:
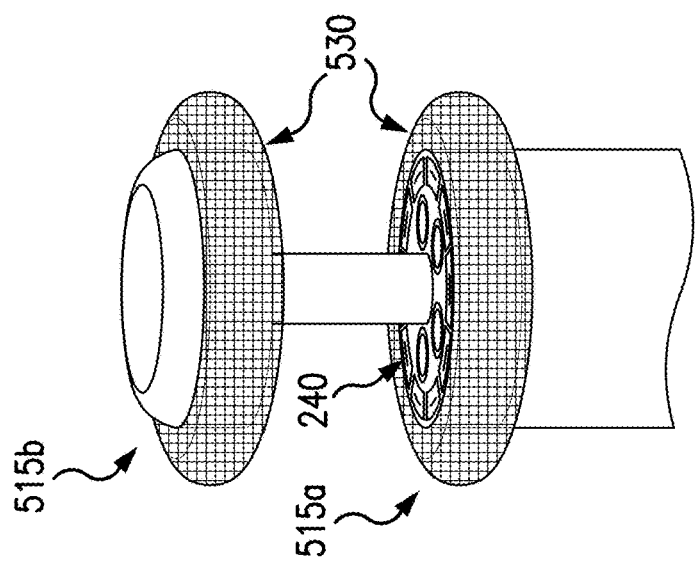
FIGS. 5A-5C illustrate exemplary embodiments of an anchoring mechanism in accordance with the present disclosure.
Figure 5B:
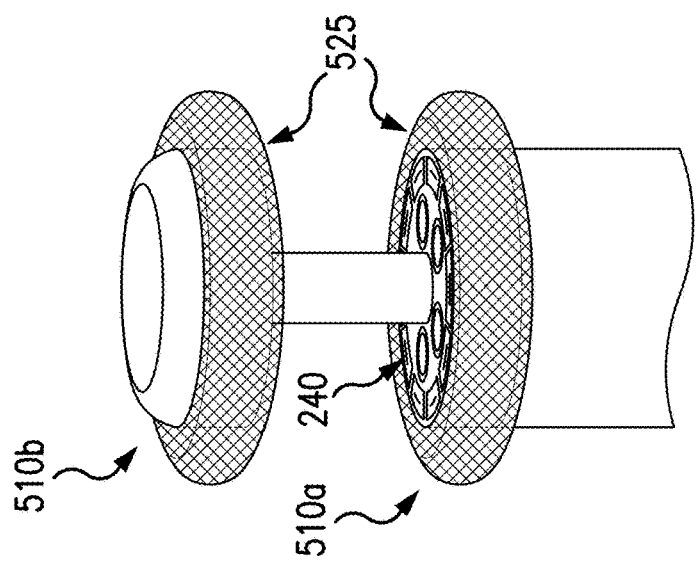
Figure 5A:
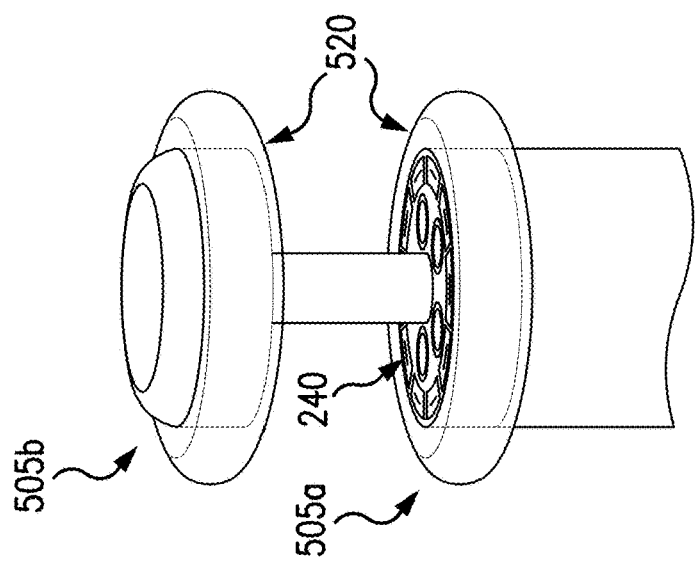

As described below, the anchoring mechanism, e.g., first and second balloons 220a, 220b, may surround and/or encapsulate a selected tissue portion site. For example, the first and second balloons 220a, 220b may engage the body 205 and the distal cap 217 proximate a selected tissue for resection in the body lumen. the first and second balloons 220a, 220b may be positioned a distance "d" apart from each other. When the first and second balloons 220a, 220b are in the desired site or position, the balloons may be expanded radially with respect to axis 202 to fill the body lumen and contact the inner surface of the body lumen. The expanded balloons may be held by friction against the inner surface of the body lumen, and movement of the shaft 210 and/or body with the balloons 220a, 220b in an expanded configuration may pleat or otherwise fold the selected diseased tissue and isolate the selected tissue. In some embodiments, the balloons 220a, 220b may be formed of a material to maximize frictional contact with a body lumen. It is envisioned that the first and/or second balloons may be formed of a same or similar material and in some embodiments may be formed of different materials. It is understood that the balloons 505a, 505b, 510a, 510b, 515a, 515b may be formed of any combination of materials. As shown in FIG. 5A, a first and/or second balloon 505a, 505b may be formed of a material 520 having a smooth elastic surface. FIG. 5B, illustrates a first and/or second balloon 510a, 510b being formed of a material 525 having a texturized elastic surface. FIG. 5C shows a first and/or second balloon 515a, 515b having a mesh covered surface 530. The mesh covered surface 530 may be an integrally formed material of the balloon 515a, 515b, and in other embodiments, may be a separate cover over a balloon 515a, 515b formed of a different material.

In some embodiments, the anchoring mechanism 215 may include tracking devices, to ensure accurate positioning in the body lumen. For example, a device 300 may include one or more markers 305 on an anchoring mechanism 215. As shown in FIG. 3, the first balloon 220a may include a first marker 305a, and the second balloon 220b may include a second marker 305b. It is understood that any number "n" of markers 305a, 305b, . . . 305n may be used in combination with any number "n" of balloons 220a, 220b, . . . 220n and/or anchoring mechanism 215. The first marker 305a may be disposed on the first balloon 220a so that when the shaft 210 and the distal cap 217 is extended out from the body 205, the second marker 305b disposed on the second balloon 220b is a distance "d" apart.

In embodiments, the one or more markers 305 may be a radiopaque marker and/or an echogenic marker. A medical professional may guide the device 200, 300 in a body lumen of a patient to a desired position using direct visualization, fluoroscopy imaging and/or ultrasound-guided navigation via the one or more markers 305. It may be advantageous to use the one or more markers 305 to ensure accurate positioning in the patient. The medical professional may desire to resect diseased tissue as well as a portion of healthy tissue surrounding the diseased tissue, to ensure full resection of any cancerous cells. Accurate positioning of the device 200, 300, e.g., selecting an accurate distance "d" may allow the medical professional to minimize the amount of healthy tissue required for resection.

Referring back to FIG. 2, in some embodiments, the device 200 may further include one or more working channels 225 for extending additional accessories 230 to the site. For example, a visualization device such as a camera, fiber optic cable, and/or other imaging device, or an endoscope, may be delivered to the desired position, although any other accessories for use during the procedure, including but not limited to lighting devices, grasping tools, fluid delivery devices, suction devices and the like may utilize the working channels 225. The accessory may be controlled and/or actuated by the medical professional at the proximal end 205a of the device 200. In some embodiments, the accessory may lock on the handle to maintain a selected position while the medical professional is free to manipulate other accessories and/or adjust the device 200 to ensure the diseased tissue is selected for resection.

Figure 4B:
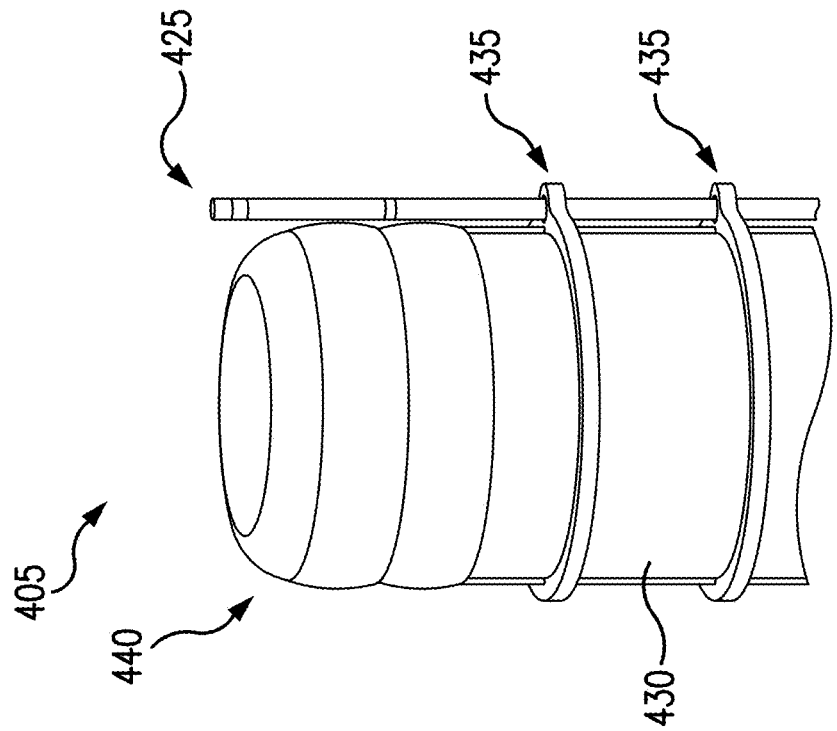
FIGS. 4A-4B illustrate exemplary embodiments of a tissue resection device and a visualization device in accordance with the present disclosure.
Figure 4A:
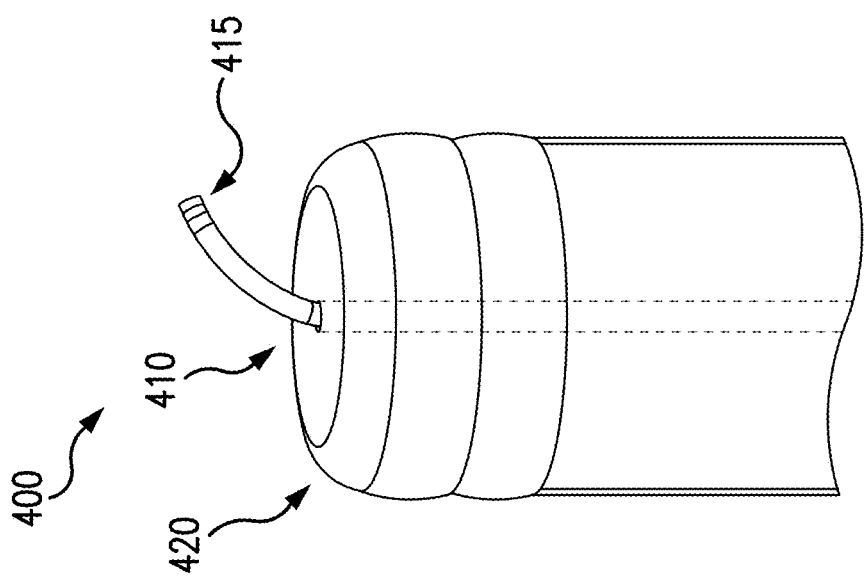

In some embodiments, the accessory may be delivered through the device 200 in various manners. As shown in FIG. 4A, a device 400 may include a working channel 410 extending along an interior of a shaft (not shown). An accessory 415 may then extend along this central working channel 410, and extend out of a distal cap 420. This may be advantageous so that an accessory, e.g., a visualization accessory such as an endoscope or other visualization device, may be utilized when the distal cap 420 is retracted. For example, the visualization accessory may be manipulatable when the shaft is not extended so that there is no gap, or distance "d", between the first and second balloons. In other embodiments, as shown in FIG. 4B, an accessory 425, e.g., an endoscope or other visualization device, may be attachable to a device 405 on an external surface 430. For example, mechanical fasteners such as rings 435 may be coupled to the external surface 430 of the device 405, for coupling the accessory 425. This configuration may be advantageous because the accessory may be utilized both when a distal cap 440 is in an extended and/or retracted position. For example, a medical professional may be able to utilize a visualization accessory when the device 405 is being positioned in a body lumen, as well as when the distal cap 440 is being positioned relative to selected tissue for resection. It is understood that selected tissue for resection may be an area of diseased tissue, e.g., including tumors and/or lesions, as well as a portion of healthy tissue immediately adjacent the diseased tissue. In some embodiments, the selected tissue for resection may include a benign cyst or legion. A portion of healthy tissue may be resected to minimize a risk of not fully capturing the diseased tissue and/or dislodging diseased tissue cells to potentially contaminate another tissue region.

Referring back to FIG. 2, in some embodiments, the device 200 may further include a tissue capture device 235. In some embodiments, a tissue capture device may be a suction device, mechanical grasping tool, and/or additional components for capturing tissue. For example, suction may be applied to grasp the tissue, and/or may be used in combination with an accessory 230 such as a mechanical grasping tool, so that tissue (e.g., the diseased tissue portion) may be engaged and held (e.g., grasped and/or sucked) inward towards the center of the body 205. When the selected tissue is grasped and held between the balloons 220a, 220b, the tissue capture device 235 may be extended to hold the tissue in place. In some embodiments, one or more posts may be extended from the body (see FIG. 8G) for capturing the tissue. The posts may extend from the body 205 parallel to the axis 202. The posts may be disposed in a circumferential pattern around the body 205, and may be actuatable individually, so that tissue may be captured between the post and the distal cap 217.

In some embodiments, the device 200 may further include one or more tissue closure devices 240, for closing together the body lumen prior to the diseased tissue being resected. In embodiments, the tissue closure device 240 may be a stapler, although other types of closure systems are also envisioned. In some embodiments, the tissue closure device 240 may be part of the tissue capture device 235. For example, when the posts extend toward the distal cap 217 to capture the tissue, a staple may be deployed from the distal cap 217 and/or the tissue capture device 235 or other portion of the body, e.g., a portion within the perimeter of the capture line with capture device or other portion of the body, e.g., a portion within the perimeter of the capture line with capture device and outside of the resecting line (e.g., cut line in the case of a blade) of the resecting device. The staple may conform to a closed shaped by forces against the tissue capture device 235 and/or the distal cap 217, to secure the selected tissue.

The device 200 may further include one or more tissue resecting devices 245, for detaching the diseased tissue. As described below (see FIGS. 6A-7C), tissue resecting devices 245 may be one or more blades, knives, cutting tool, cauterizing tool, or the like, and may be configured to extend from the body 205 once the device 200 is in position and the selected tissue is positioned for resection. For example, in embodiments, one or more blades may be extendable in a direction parallel to the axis 202, e.g., from the proximal portion of the distal end 205b of the body 205 towards the distal portion of the distal end 205b of the body 205. The blades may be movable circumferentially around the body 205, e.g., to resect the selected tissue internal to the stapled portion, or may be a punch or cookie cutter configuration that resects a full circumference in one movement. It may be advantageous to resect the selected tissue after staples are deployed to secure the selected tissue, to prevent undesired tissue separation. It is also envisioned that in other embodiments, the tissue resecting device 245 may resect the tissue prior to the tissue closure device 240 securing the tissue.

Figure 6B:
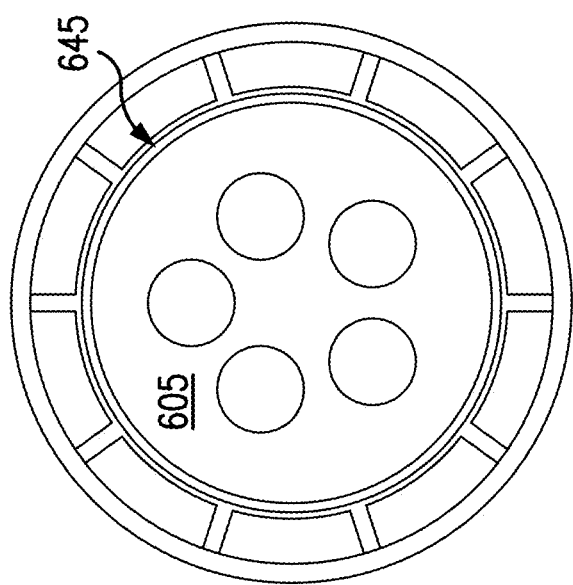
FIGS. 6A-6B illustrate exemplary embodiments of a tissue resecting device of a tissue resection device in accordance with the present disclosure.
Figure 6A:
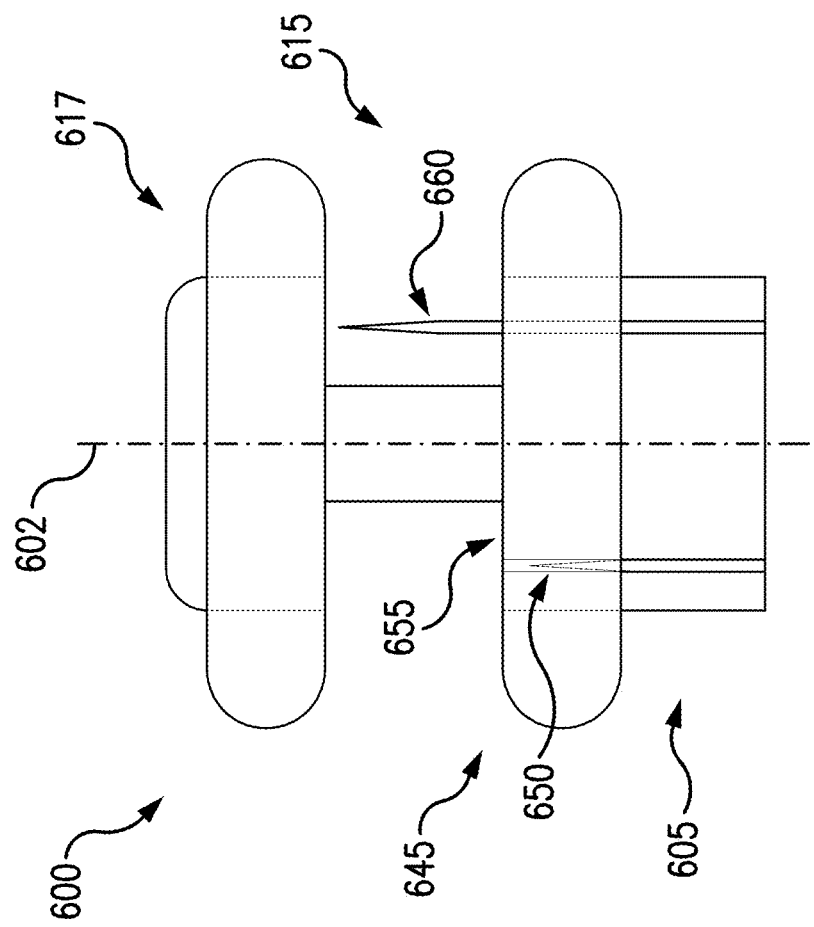

As shown in FIGS. 6A-6B, a resection device 600 may include a tissue resecting device 645 extending from a body 605 in a direction parallel to axis 602. In embodiments, the tissue resecting device 645 may be circumferential to the body 605, so that tissue selected for resection may be resected when positioned between the anchoring mechanism 615. For example, the anchoring mechanism may engage tissue proximate the selected tissue for resection. In embodiments, the tissue resecting device 645 may be in a retracted position, as shown at reference numeral 650. In a retracted position, the tissue resecting device 645 may be fully retracted within the body 605 (e.g., below a surface 655), so that no tissue may be resected. In an extended position, as shown at reference number 660, the tissue resecting device 645 may be extended from the surface 655 of the body 605 toward the distal cap 617. As described above, one or more tissue capture devices may hold the selected tissue for resection against the distal cap 617. Once the tissue is secured by the tissue capture devices, the tissue resecting device 645 may extend, resecting the selected tissue for resection. In some embodiments, the tissue resecting device 645 may be a single blade, disposed circumferentially in the body 605, which may be actuatable in a single motion. In other embodiments, a plurality of tissue devices may be utilized, disposed and actuatable individually around the body 605.

Figure 7C:
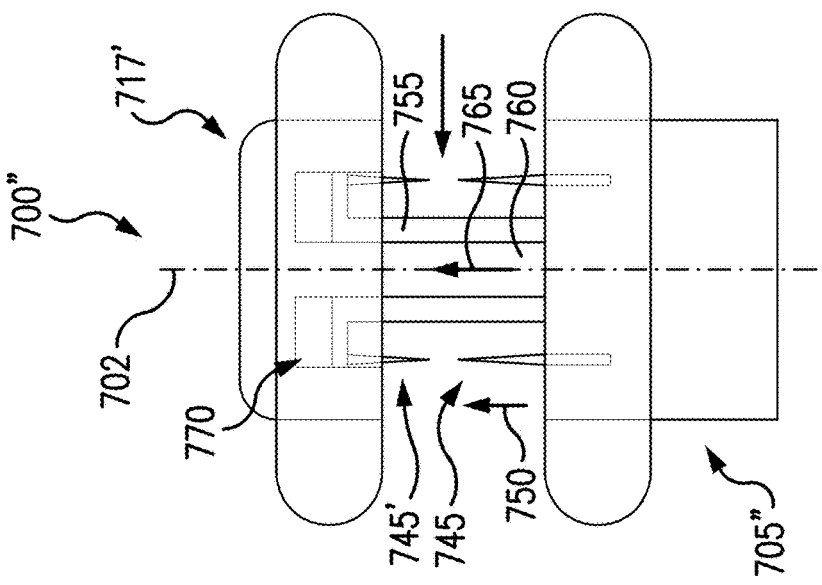
FIGS. 7A-7C illustrate exemplary embodiments of a tissue resecting device of a tissue resection device in accordance with the present disclosure.
Figure 7B:
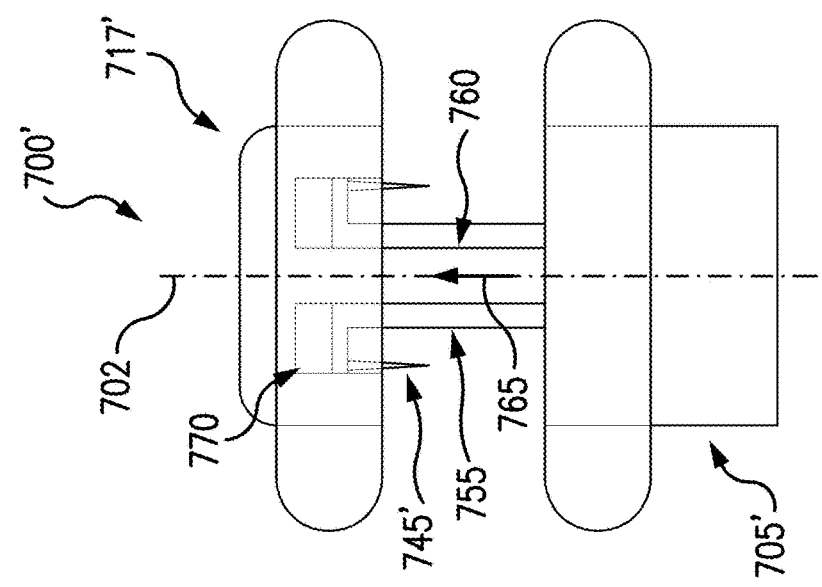
Figure 7A:
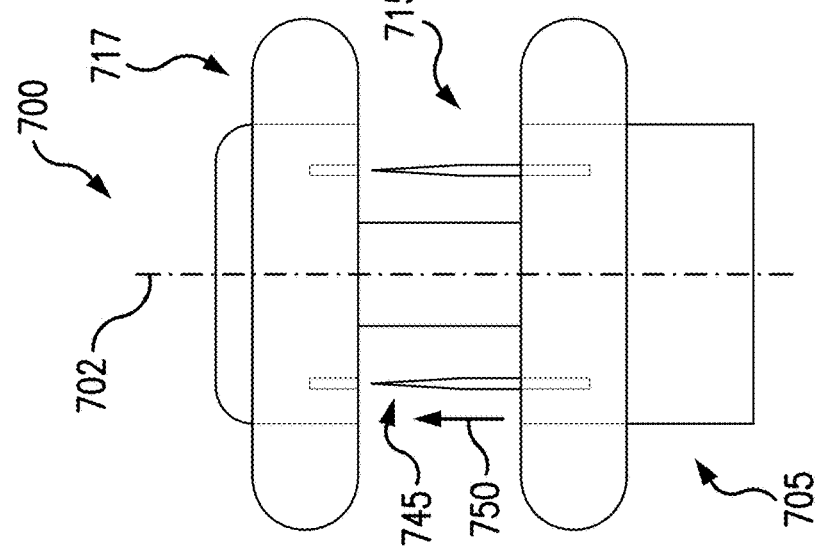

Additionally, it is envisioned that a tissue resecting device may extend from the body 605, 705, as shown in FIGS. 6A-6B and 7A, and/or the distal cap 617, 717, as shown in FIGS. 7B-7C. The tissue resecting device 645, 745, 745' may be the same or similar tools as the tissue resecting device 245 in FIG. 2. In embodiments where the tissue resecting device 245, 645, 745, 745' is a blade, the blade may be formed in any shape, including but not limited to a straight blade edge, a tapered blade edge, crenellated, and/or saw tooth. For example, a tissue resecting device 745 may extend from the body 705 in a direction indicated by arrow 750.

The tissue resecting device 745 may be extendable and/or retractable in a direction parallel to axis 702. In other embodiments, a tissue resecting device 745' may be disposed in the distal cap 717'. The tissue resecting device 745' may be extendable and/or retractable by an outer shaft 755, in which the tissue resecting device 745' is coupled to, and an inner shaft 760, which is coupled to the distal cap 717'. In a retracted position, the tissue resecting device 745' may be nested in a gap 770 in the distal cap 717'. To expose the tissue resecting device 745', the inner shaft 760 may move in a distal direction, e.g., as shown by arrow 765, while the outer shaft 755 and tissue resecting device 745' remain stationary. In some embodiments, the inner shaft 760 may remain stationary while the outer shaft 755 and tissue resecting device 745' move in a proximal direction toward the body 705. In other embodiments, the inner shaft 760 may move in a distal direction and the outer shaft 755 and tissue resecting device 745' may move in a proximal direction.

FIG. 7C illustrates a combination of the features described in FIGS. 7A-7B. For example, the device 700" may include a tissue resecting device 745 disposed in body 705, and a tissue resecting device 745' disposed in the distal cap 717'. The tissue resecting devices 745, 745' may be able to resect the selected tissue for resection from both directions, e.g., the tissue resecting device 745 may extend in a distal direction from the body 705, and the tissue resecting device 745' may extend in a proximal direction from the distal cap 717'. In embodiments where the tissue resecting devices 745, 745' are blades, the blades may be formed in any shaped as described above, and in some embodiments may be configured to mate together.

Referring now to FIGS. 8A-8J, a process of tissue resection by an exemplary embodiment of a tissue resection device 800 in accordance with the present disclosure is shown. It is understood that any of the features described in the exemplary embodiments illustrated in FIGS. 2-7C may also be incorporated in the device 800. At step 805*a*, a scope, e.g., an endoscope, gastroscope, colonoscope, duodenoscope, and the like, may be inserted in a patient and delivered to a body lumen 815 having tissue for resection. In some embodiments, a visualization device 810, e.g., an accessory such as a camera, fiber optic or other device, may be used for visualizing the tissue for resection. The device 810 may extend in the body lumen 815 in a direction along axis 802. As described above, the tissue may have tumors, lesions and/or otherwise may be diseased. A medical professional may mark the tissue for resection, e.g., indicated by arrow 820. Tissue may be marked by ink, radiopaque contrast, echogenic contrast, or other known techniques. In some embodiments, a medical professional may utilize fluoroscopy imaging and/or ultrasound guided navigation techniques for visualizing the tissue selected for resection. The tissue for resection may be marked as two circumferential bands, e.g., 825*a*, 825*b*, to bound the area of tissue for resection. It is understood that when tissue is resected from the body lumen 815, it may be fully resected, so that the body lumen is separated into two portions. To prevent edges of the body lumen 815, e.g., at bounds of markers 825*a*, 825*b*, from separating, tissue closure devices such as staples and/or adhesive may be used to join the edges of the body lumen 815. This may minimize and/or prevent contamination of the body lumen 815 from surrounding body fluids.

Figure 8C:
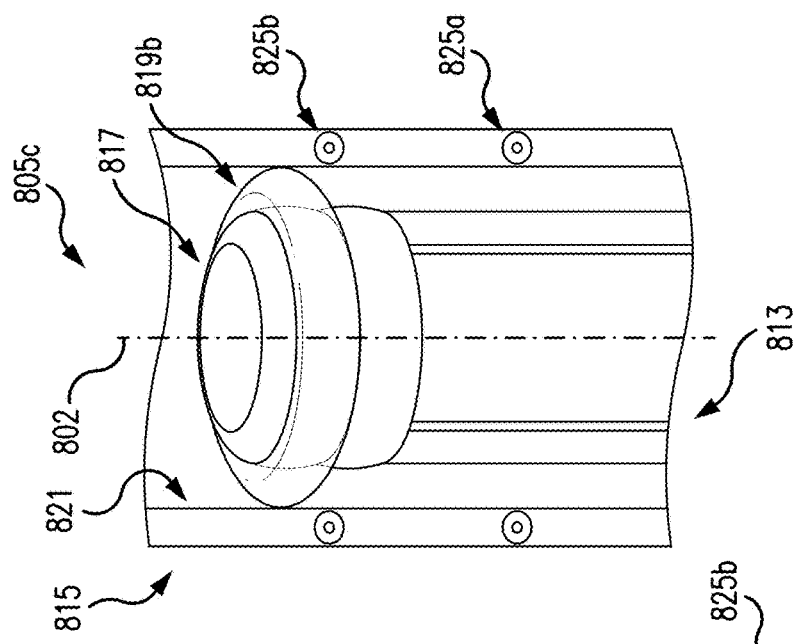
FIGS. 8A-8J illustrate an exemplary process for resecting tissue using a tissue resection device in accordance with the present disclosure.
Figure 8B:
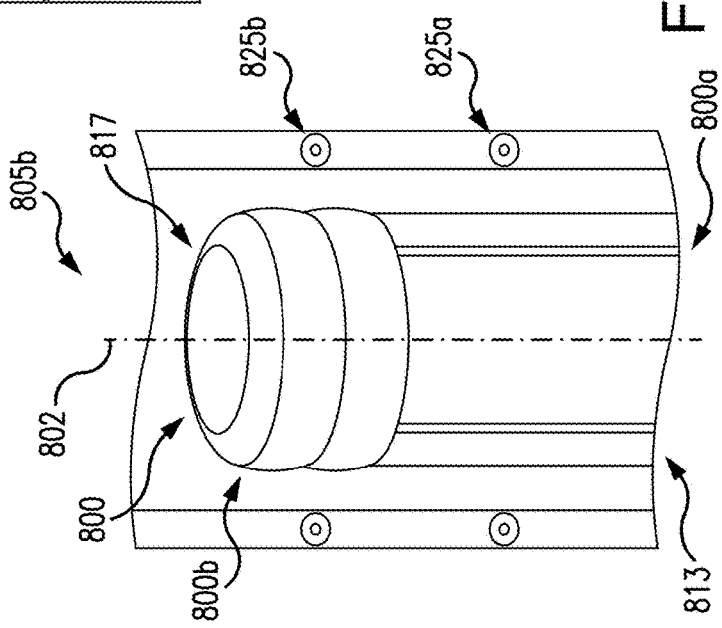
Figure 8A:
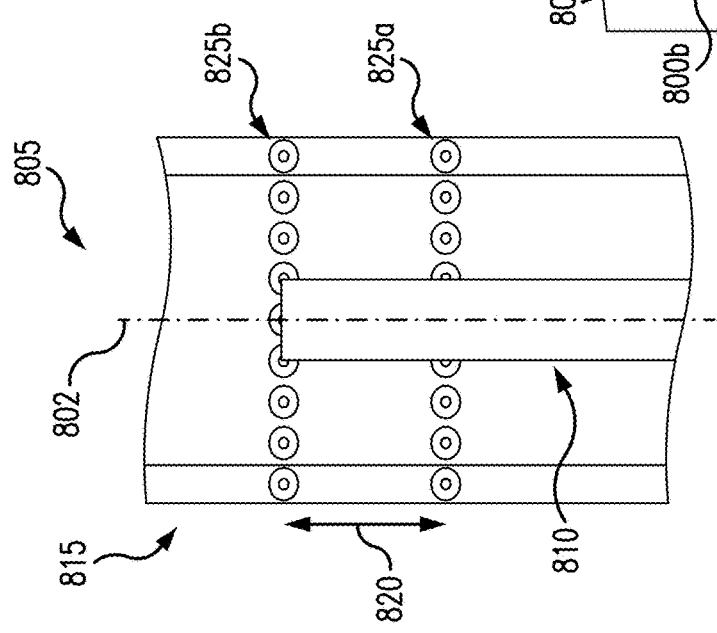
Figure 8E:
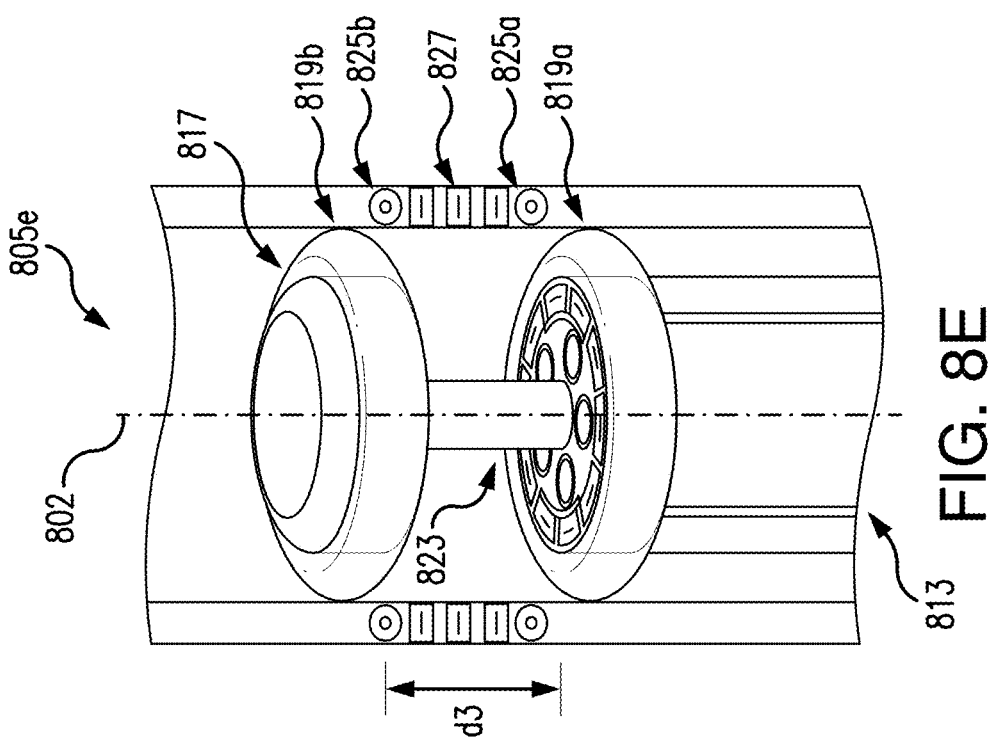

At step 805*b*, as shown in FIG. 8B, the device 810 may be removed from the patient, and a tissue resection device 800 having a proximal end 800*a* and a distal end 800*b* and formed of a body 813 may be inserted and delivered to the body lumen 815 to the tissue marked for resection. The distal end 800*b* of the device 800 may have a distal cap 817 and may be positioned distal of the tissue marked for resection (the second marker band 825*b*). It may be understood that the proximal end 800*a* of the device 800 may be external to a patient, and the distal end 800*b* of the device 800 may be at the site for tissue resection. At step 805*c*, as shown in FIG. 8C, an anchoring mechanism such as a balloon 819*b* may be expanded to anchor the device 800 to the body lumen 815. The balloon 819*b* may be disposed on the distal cap 817, and the balloon 819*b* may contact an inner surface 821 of the body lumen 815, e.g., in an area distal of the tissue marked for resection by markers 825*a*, 825*b*. The balloon 819*b* may be expandable in a radial direction relative to the axis 802.

Figure 8D:
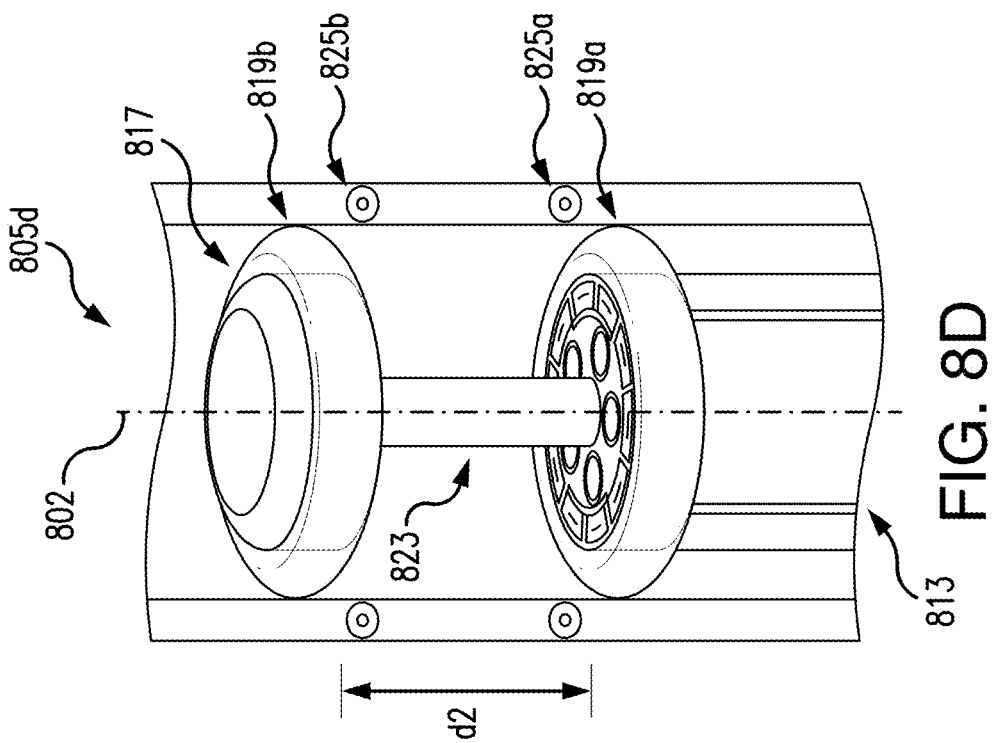
Figure 8G:
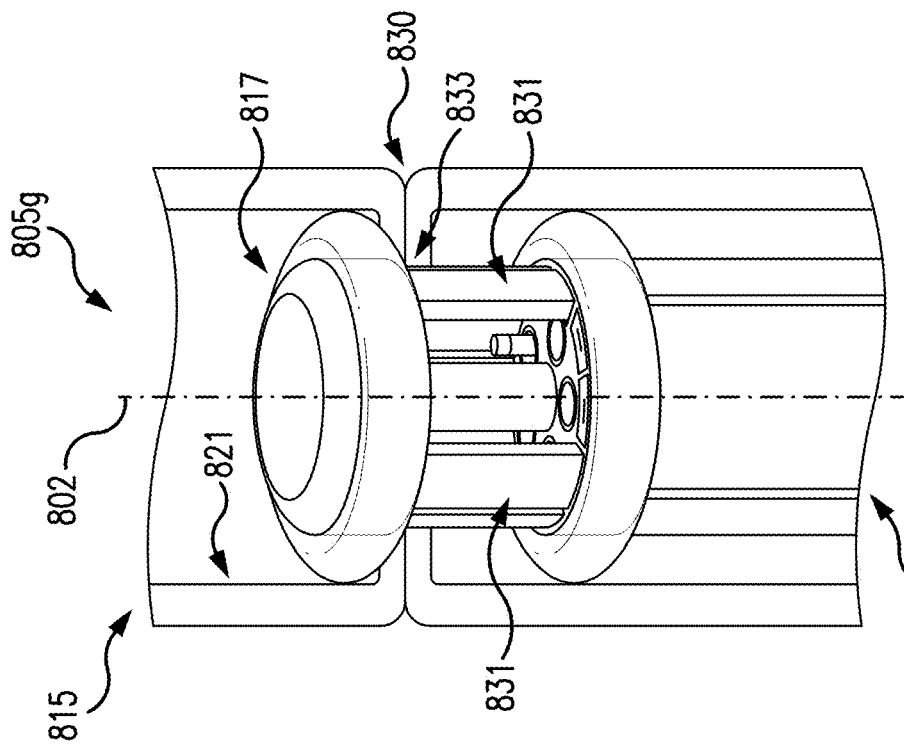

At step 805*d*, as shown in FIG. 8D, the device 800 may be extended so that the anchoring mechanism encompasses the tissue for resection as bounded by markers 825*a*, 825*b*. For example, the anchoring mechanism may engage tissue proximate the selected tissue for resection in the body lumen. As described above, a shaft 823 may be connected to the distal cap 817, and may be movable along the axis 802 relative to the body 813. In some embodiments, the body 813 may be movable relative to the shaft 823 and/or the distal cap 817. For example, when the balloon 819*b* is expanded to anchor the distal cap 817 to the inner surface 821 of the body lumen 815, the body 813 may move in a proximal direction away from the distal cap 817 and exposing the shaft 823. The body 813 may be positionable to an area in the body lumen outside of the bounds of (e.g., proximal to) the marked tissue by markers 825*a*, 825*b*. A balloon 819*a* may be expanded to anchor the device 800 to the body lumen 815. The body 813 and the distal cap 817 may be separated by a distance "d2", along the axis 802, which may correspond to the selected tissue for resection, e.g., between markers 825*a*, 825*b*.

At step 805*e*, as shown in FIG. 8E, the distal cap 817 and/or the body 813 may be drawn together, to compress the tissue selected for resection between markers 825*a*, 825*b*. For example, the distal cap 817 may be moved in a proximal direction while the body 813 remains stationary, the body 813 may be moved in a distal direction while the distal cap 817 remains stationary, or both the body 813 and the distal cap 817 may be movable. It is understood that when the distal cap 817 and or the body 813 are moved with the balloons 819*a*, 819*b* in an expanded condition, friction between the respective balloon 819*a*, 819*b*, and the inner surface 821 of the body lumen 815 may minimize and/or prevent slippage of the balloon 819*a*, 819*b* so that the tissue selected for resection may become pleated as indicated at reference numeral 827, and a distance "d3" between the body 813 and the distal cap 817 is less than the distance "d2" as shown in FIG. 8D.

Figure 8F:
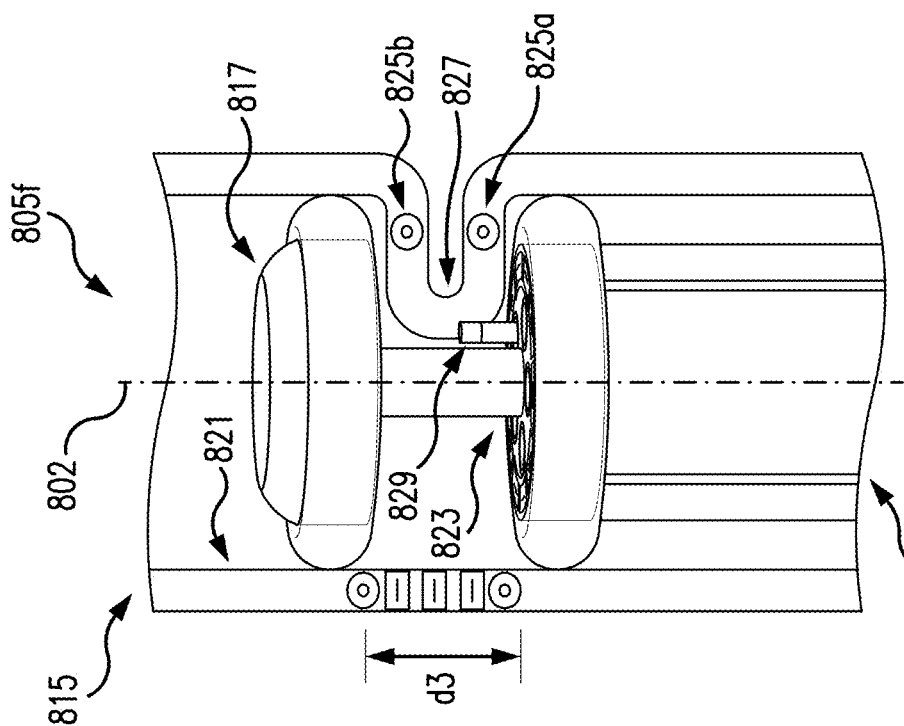

At step 805*f*, as shown in FIG. 8F, the pleated tissue 827, e.g., the tissue for resection, may be drawn radially inward towards the shaft 823. In some embodiments, an accessory 829 such as a suction device or mechanical grasper tool may be utilized as a tissue capture device. The accessory may be movable in a circumferential direction to rotate about the axis 802, pulling the selected tissue for resection inward until the entire circumferential section is drawn inward. As described above, this procedure may be advantageous for full thickness resection, e.g., resecting all tissue layers from a portion of a body lumen. At step 805*g* (see FIG. 8G), one or more tissue capture devices 831 may extend from the body 813 in a distal direction to capture and hold the tissue selected for resection against an inner surface 833 of the distal cap 817, as indicated at reference numeral 830. The tissue capture devices 831 may be disposed circumferentially around the device 800 with respect to axis 802. In embodiments, the tissue pulled in by the accessory may be captured in the tissue capture device as each section of circumference of tissue is pulled in or the entire circumference of tissue may be pulled in before the capturing device is actuated. In embodiments, the tissue capture devices 831 may be posts, e.g., having a blunt distal ends to hold the tissue in place without damaging the tissue.

In some embodiments, when the posts extend to the distal cap 817, a tissue closure device may close, or seal off the tissue bounded by markers 825a, 825b. For example, staples 840 may be delivered circumferentially against the posts to secure the tissue, e.g., bounding the tissue for resection by the markers 825a, 825b (see FIG. 8J). In other embodiments, adhesive or other closure mechanisms may be used to secure the tissue. In some embodiments, staples may be pre-loaded in the body 813 and the distal cap 817 may comprise or incorporate a forming anvil. When the body 813 and the cap 817 are closed, forces exerted on the staples as they are pressed into the anvil may close the staples around the tissue. In embodiments, a plurality of staples may be stapled simultaneously with an axially translated clamping mechanism or staple driving mechanism, e.g., as the body 813 and the distal cap 817 are moved together along the axis 802. In other embodiments, a plurality of staples may be stapled sequentially, e.g., by a rotating wedge clamping or staple driving mechanism, thereby forming the staples one at a time as the wedge mechanism is rotated about the circumference of the body 813 and the wedge sequentially contacts, drives, and forms each staple. Such a mechanism may require reduced staple forming forces compared to other forming mechanisms and techniques. In some embodiments, staples may be pre-loaded in the distal cap 817, with the body 813 acting as the forming anvil, and the staples may be spring-loaded, or hydraulically actuatable, or combinations thereof. Alternatively, a simultaneous or sequential (e.g., wedge) driver mechanism may be employed. The tissue capture device 831, e.g., posts, may temporarily hold the tissue prior to stapling. The medical professional may be able to verify with tissue markers prior to stapling and/or resecting that the selected tissue for resection encompasses all of the desired tissue for resection, and may make adjustments as necessary. The tissue capture devices 831, e.g., posts, may include tissue closure devices 240, which may be forming anvils. As staples are deployed, staples may be formed by forces acting against the forming anvil to enclose the selected tissue for resection with the staples.

Figure 8J:
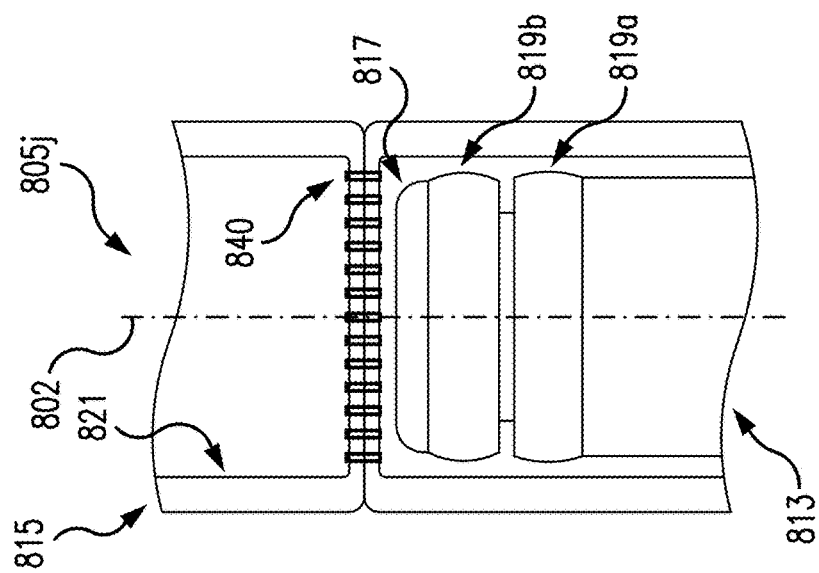
Figure 8I:
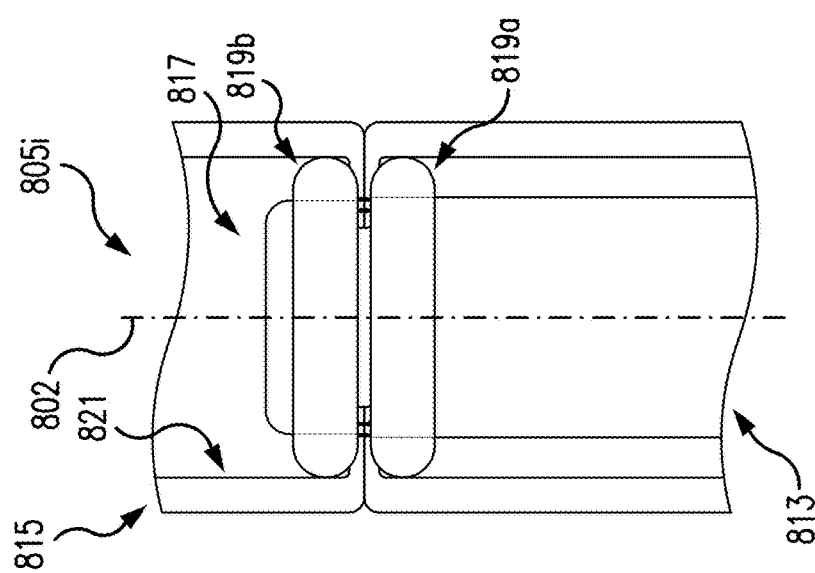
Figure 8H:
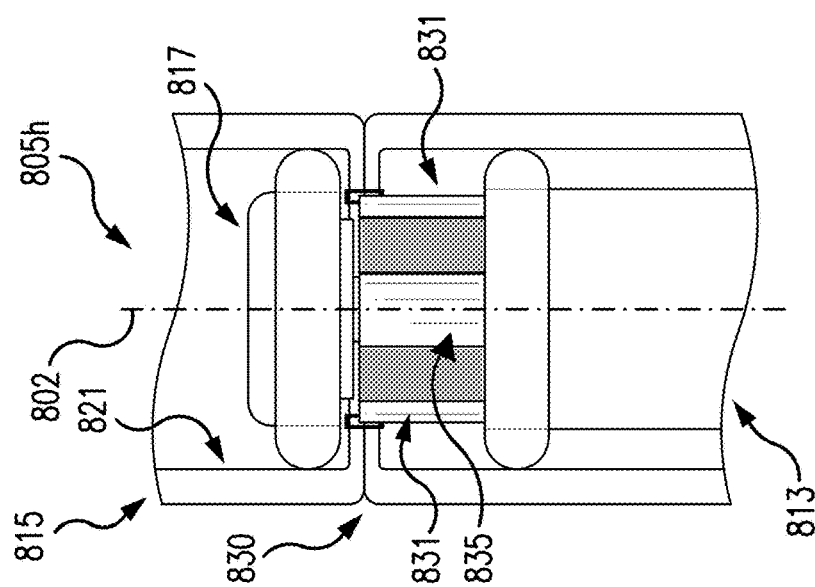

When the tissue is secured by the tissue capture devices 831 and/or the tissue closure device, at step 805h and as shown in FIG. 8H, a tissue resecting device 835 may be extended from the body 813 and/or the distal cap 817. As described above with respect to FIGS. 2 and 6A-7C, a tissue resecting device may be disposed circumferentially around the body 813 and/or distal cap 817 about the axis 802. In embodiments, the tissue resecting device 835 may be positioned radially inward from the tissue capture device 831 and/or the tissue closure device, so that as the tissue is resected, the secured tissue is held by the tissue capture device 831 and/or staples of the tissue closure device. In this manner, the resected portion of the body lumen 815 may be prevented from separating during the procedure. At step 805i as shown in FIG. 8I, when the tissue is resected or otherwise cut, the distal cap 817 and the body 813 may be drawn together. The tissue capture device 831 and/or the tissue closure device may be retracted. The resected tissue may be removed from the patient through a working channel (see FIG. 2), e.g., by a mechanical grasping tool or other retrieval device.

At step 805j as shown in FIG. 8J, when the procedure is complete, the balloons 819a, 819b may be deflated, so the device 800 is no longer anchored to the inner surface 821 of the body lumen 815. The device 800 may then be removed from the patient, e.g., retracted proximally from the body lumen 815. Staples 840, or other closure mechanisms such as a suture and/or adhesive, may secure ends of the body lumen 815 from the tissue bounded by markers 825a, 825b. In embodiments, the closure mechanisms may be formed of a material that is bioabsorbable and/or biodegradable. As tissue regrowth occurs the closure mechanisms may naturally degrade. In some embodiments, the closure mechanisms may be removable from the patient.

Figure 9A:
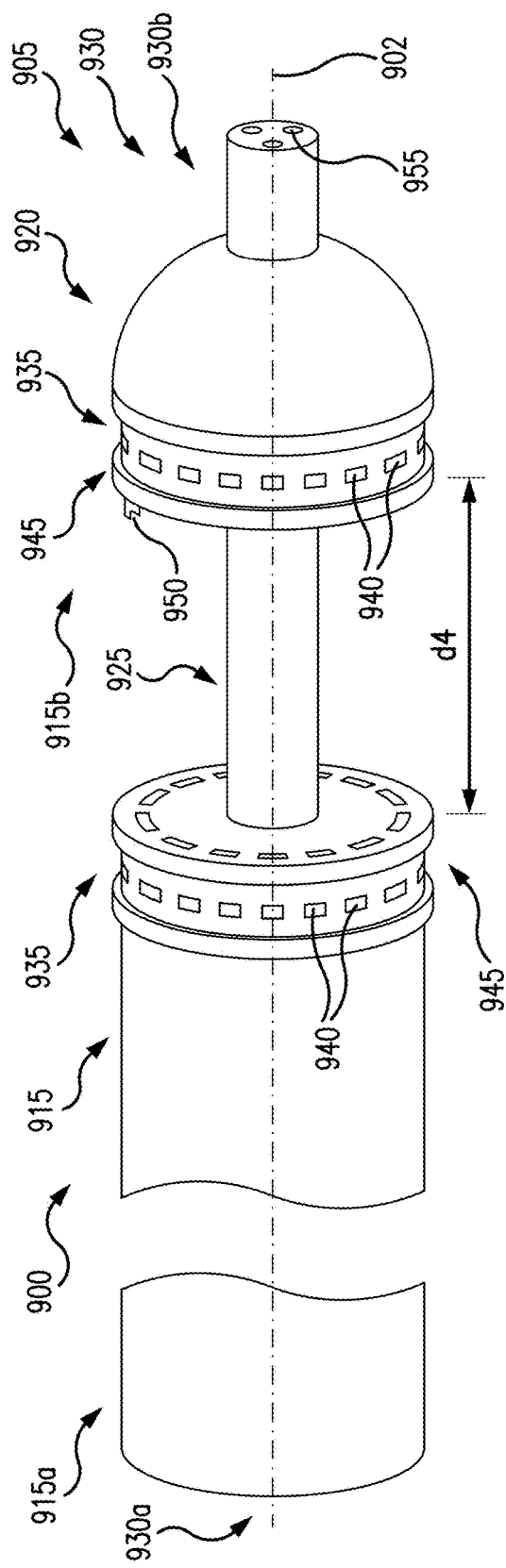
FIGS. 9A-9B illustrate an exemplary tissue resection device in accordance with the present disclosure.
Figure 9B:
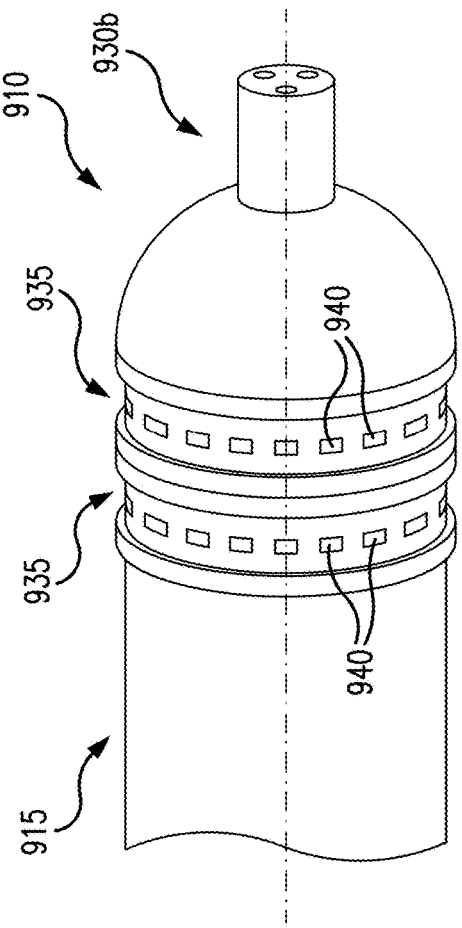

Referring now to FIGS. 9A-9B, another exemplary embodiment of a tissue resection device 900 in accordance with the present disclosure, is shown. At FIG. 9A, the device 900 is shown in an extended position 905, and FIG. 9B shows the device 900 in a retracted position 910.

The device 900 may include a body portion 915 and a distal cap portion 920. The body 915 may be a tubular shape, extending along axis 902, and the distal cap 920 may be coupled to a shaft 925 movable along the axis 902. The shaft 925 may be coaxial to the body 915 along axis 902. In embodiments, the distal cap 920 may be at least partially spherical, e.g., dome-shaped, and coaxial to the body 915 and shaft 925. The shaft 925 may be movable relative to the body 915, so that the distal cap 920 and the body 915 may be formed a distance "d4" apart from each other for receiving tissue to be resected, e.g., similar to the embodiments described in FIGS. 2-8J.

The device 900 may be configured to extend along an exterior surface of a scope 930, e.g., an endoscope, colonoscope, gastroscope, and/or duodenoscope. For example, a distal end 930b of the scope 930 may be first positioned in a body lumen at the desired position, with a proximal end 930a being external to the patient. The device 900 may then be delivered to the distal end 930b. In embodiments, the scope 930 may be internal to shaft 925 of the device 900. In embodiments, the scope 930 may have a visualization device 955 (e.g., a camera, fiber optic cable, and the like). In embodiments, the visualization device 955 may be disposed on a distal end of the scope 930, although it is envisioned that the visualization device 955 may be disposed on a side portion of the scope 930. In some embodiments a visualization device independent of the scope 930 may be used for visualizing the positioning of the device 900.

Figure 10C:
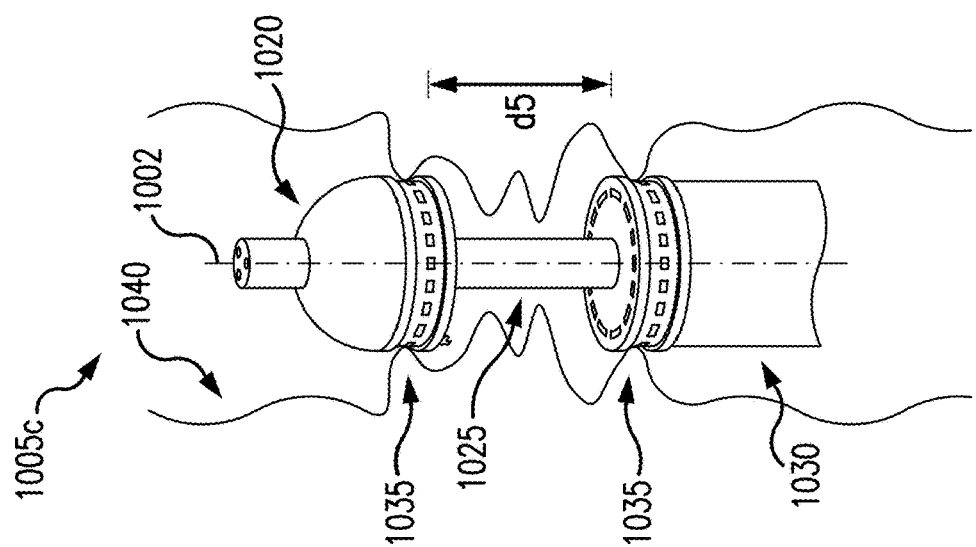
Figure 10B:
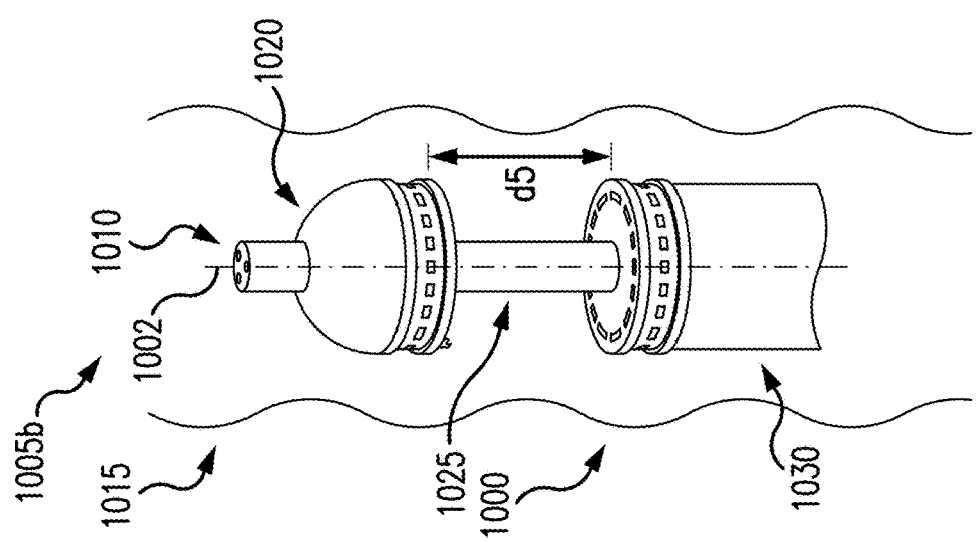

In embodiments, when the device 900 is delivered to the body lumen of the patient, the device 900 may be anchored to an inner surface of the body lumen by suction, e.g., by an anchoring mechanism 935. The anchoring mechanism 935 may be in the body 915 and/or the distal cap 920, for engaging body lumen tissue. In some embodiments, the anchoring mechanism 935 may be configured to have a plurality of suction channels 940, extending around an outer circumference 945 of the body 915 and/or the distal cap 920. A vacuum may initiate suction by drawing in and holding the tissue at the body 915 and/or the distal cap 920 as a tissue capture device (see FIG. 10C). It is also understood that other attachment mechanisms may be used as an anchoring mechanism 935 to engage the distal cap 920 and/or the body 915 to an inner surface of the body lumen. For example, mechanical fasteners such as hooks, needles (e.g., j-shaped needles) suture, and/or T-tags may be configured to extend radially from openings on an outer circumference 945 of the distal cap 920 and/or the body 915 to anchor the device 900. The mechanical fasteners may extend circumferentially to engage the body lumen.

Figure 10A:
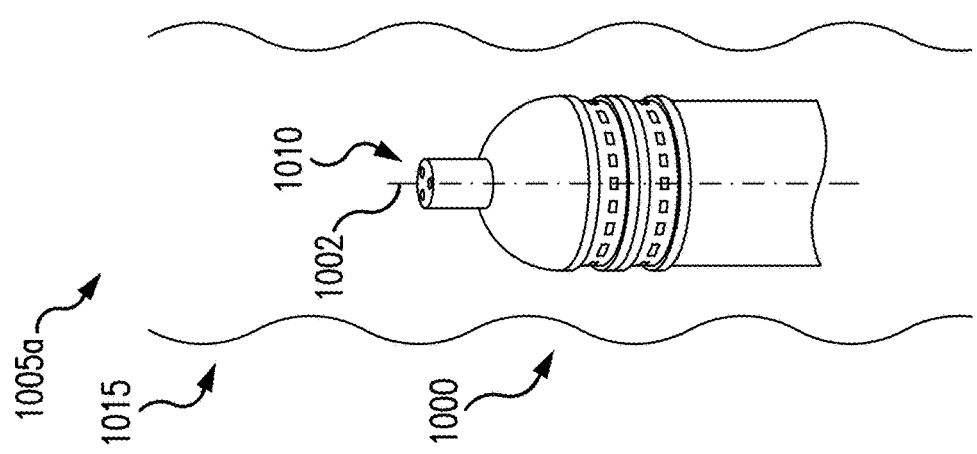
Figure 13B:
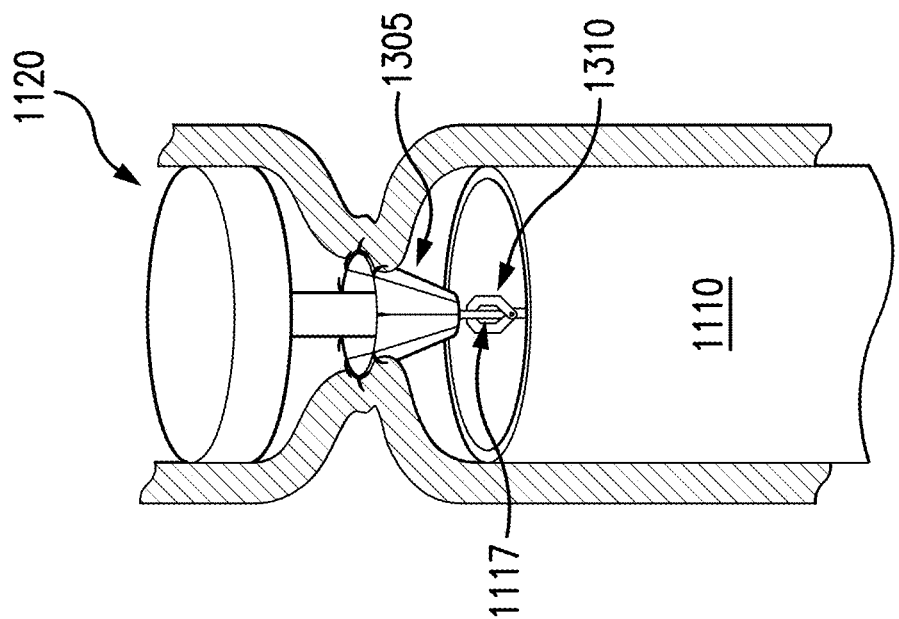
FIGS. 13A-13B illustrate an exemplary tissue resection device and process for resecting tissue in accordance with the present disclosure.
Figure 13A:
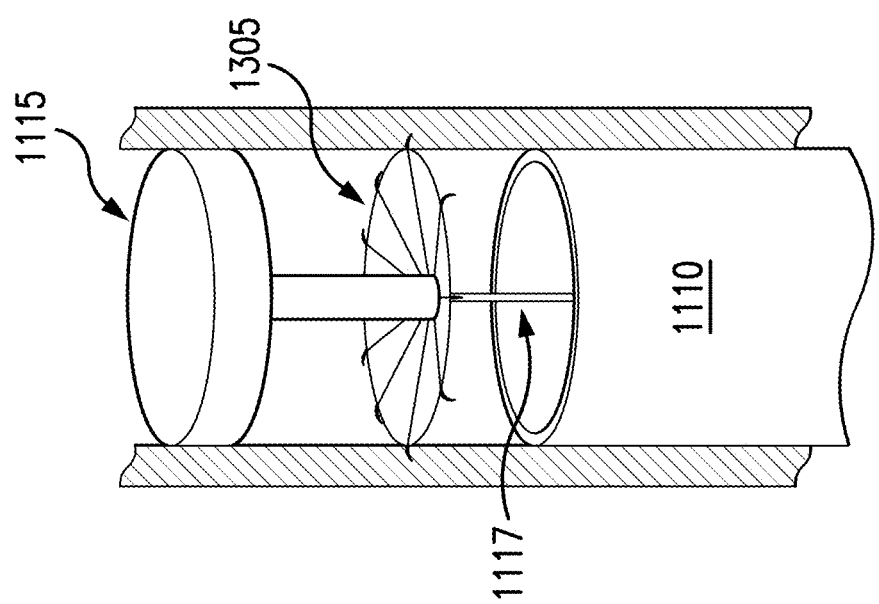

Referring now to FIGS. 10A-10E, a process for resecting tissue using an exemplary embodiment of a tissue resection device 1000 in accordance with the present disclosure. It is understood that any of the features described in FIGS. 2-9B may be included in the device 1000. At step 1005a as shown in FIG. 10A, an endoscope 1010 may be delivered to a body lumen 1015 having a tissue section for resection. As described above, a full thickness tissue portion may be resected by circumferentially resecting a selected tissue of the body lumen 1015. When the endoscope 1010 is in the desired position, e.g., the medical professional has visually determined the tissue for resection by the endoscope 1010, the device 1000 may be extended to an open position. As shown at step 1005b in FIG. 10B, the distal cap 1020 and/or the body 1030 may be extended by the shaft 1025 so that the distal cap 1020 and the body 1030 are spaced a distance "d5" apart. The distance "d5" may encompass tissue of the body lumen 1015 selected for resection.

When the device 1000 is positioned as desired, suction may be initiated by the suction device 1035 in the body 1030 and/or the distal cap 1020 as a tissue capture device. An inner surface 1040 of the body lumen 1015 may be drawn toward and engaged with the suction device 1035. In some embodiments, a plurality of suction channels 1037 may engage the inner surface 1040 of the body lumen 1015 so that an entire circumferential portion of the body lumen is engaged with the device 1000. In embodiments, a suction device 1035 may be disposed in both the distal cap 1020 and the body 1030, so that tissue selected for resection may be bounded by a distal portion of tissue engaged with the distal cap 1020, and a proximal portion of tissue engaged with the body 1030. When the device 1000 is engaged with the distal cap 1020 and the body 1030, the device 1000 may be engaged, or anchored, to the body lumen 1015.

At step 1005d as shown in FIGS. 10D-10E, the distal cap 1020 and the body 1030 may be drawn together, to gather body lumen tissue bounded by the distal and proximal engaged tissue portions as shown at reference numeral 1045. As described above in FIG. 8F, an accessory such as a mechanical grasper tool or further suction device may be utilized to draw the tissue radially inward. When the tissue selected for resection is positioned between the body 1030 and the distal cap 1020, a tissue closure device 1050 and/or a tissue resecting device 1055 may be used as described above with respect to FIGS. 8G-8J. For example, a tissue closure device 1050 may be a circular ring disposed on the distal cap 1020 and/or the body 1030, e.g., having a blunt edge. As the distal cap 1020 and/or the body 1030 are drawn together, the tissue selected for resection may be held by the tissue closure device to clamp the tissue closure device against the tissue.

When the tissue selected for resection is clamped between the distal cap 1020 and the body 1030, a tissue resecting device 1055 may be utilized to resect the selected tissue. For example, in some embodiments, a blade or other resecting device such as an electrocautery device, and/or radially expandable wire, may be extendable from the distal cap 1020 and/or the body 1030. The tissue resecting device 1055 may be movable circumferentially around the distal cap 1020 and/or the body 1030 about axis 1002. For example, the tissue resecting device 1055 may begin resecting tissue at 0° and finish resecting tissue at 360° for full tissue resection of a portion of the body lumen 1015. In embodiments, the blade may resemble a hole punch, as described above.

In some embodiments, a tissue closure device 1060 may be used to join edges of the body lumen 1015 from the portion for resection. For example, a tissue closure device 1060 may include staples, a suture, clips, and/or adhesive as a closure mechanism. The closure mechanisms may be pre-loaded in the device 1000 for deployment. The tissue closure device 1060 may be deployed circumferentially around the tissue, similar to FIGS. 8G-8J. It is understood that the tissue closure device 1060 may insert staples or other closure mechanisms prior to the tissue being resected by a tissue resecting device 1055. Sealing the body lumen prior to resecting the selected portion of tissue may minimize and/or prevent contamination of the body lumen by surrounding bodily fluid and/or the surrounding area from fluid in the body lumen. When the selected tissue for resection has been resected, the device 1000 may detach from the inner surface 1040 of the body lumen 1015, e.g., by stopping the vacuum. The device 1000 may then be removed from the patient, by retracting in a proximal direction.

Referring now to FIGS. 11A-11C, 12A-12C, and 13A-13B, another embodiment of a tissue resection device 1100, 1200 and a process for resecting tissue is shown. The device 1100, 1200 may include a body portion 1110 extending along an axis 1102. The body portion 1110 may be substantially cylindrical and in embodiments may be a hollow tube, e.g., for receiving a portion of body lumen 1120. A distal cap 1115 may be disposed distal of the body 1110 along the axis 1102, and may be substantially circular, cylindrical, or any other shape to be configured to couple with the body 1110. In some embodiments, the distal cap 1115 may be coupled to a sheath, or lumen 1117, which may be extendable along the axis 1102a and manipulatable at a proximal end (e.g., outside of the patient) for positioning relative to the body 1110. In some embodiments, the lumen 1117 may be coupled to a connector 1118 of the distal cap 1115. The connector 1118 may be integrally formed on the distal cap 1115, on a proximal side, for coupling to the lumen 1117. In some embodiments, the connector 1118 may be attached to the distal cap 1115. The body 1110 and/or the distal cap 1115 may be formed of a material such as steel, nitinol, plastic, expandable balloons, and/or any other material configured to contain the selected tissue for resection. In some embodiments, a proximal end 1110a of the body 1110 may have an opening 1220, which may be utilized for delivery of additional tools and/or devices, including but not limited to a resecting device such as a knife, an attachment tool such as a t-tag, or other components of the tissue resection device 1100, 1200. For example, a scope such as an endoscope, gastroscope, colonoscope, duodenoscope, and the like, may be receivable in the opening 1220, which may include one or more tools for tissue resection and one or more working channels.

In embodiments, the body 1110 and the distal cap 1115 may be delivered in a coupled configuration to the body lumen 1120, and the distal cap 1115 and the body 1110 may then be decoupled to position for tissue resection. For example, at step 1105a, 1205a the distal cap 1115 may be positioned in the body lumen 1120 distal of a selected tissue for resection 1125, and the body 1110 may be positioned in the body lumen 1120 proximal to the selected tissue for resection 1125, so that the body portion 1110 and the distal cap 1115 are a distance "d6" apart. In some embodiments, a medical professional may mark the tissue for resection, as described above, e.g., by ink, radiopaque contrast, echogenic contrast, or other known techniques, and/or utilizing fluoroscopy imaging and/or ultrasound guided navigation techniques for visualizing the tissue selected for resection. Additionally, a medical professional may be able to visualize positioning of the device 1100, 1200 by a visualization device such as a camera, fiber optic cable, and/or other imaging device may be delivered to the desired position.

As described above, in some embodiments, the device 1100, 1200 may be deliverable over an endoscope 1240, and a visualization device may be used by delivering to the treatment site by a working channel of the endoscope. For example, an endoscope 1240 may be extendable along the axis 1102a and receivable in the opening 1220. As shown in FIG. 12C, an endoscope 1240 may include one or more working channels for delivering the lumen 1117, a resecting device such as a knife, and/or a mechanical fastener 1225 such as a t-tag. In some embodiments, the device 1100, 1200 may be a separate accessory of an endoscope. In other embodiments, the body 1110 and the distal cap 1115 may be deliverable to a treatment site through a working channel of an endoscope, and may be extendable to fit an inner diameter of the body lumen. The lumen 1117, which in some embodiments may be a guidewire or other rigid or semi-rigid pushing tool, may allow the medical professional to articulate the body 1110 and/or the distal cap 1115. In some embodiments, the body 1110 and/or the cap 1115 may be delivered to the treatment site by being pushed over an imaging device such as an endoscope. In this fashion, the endoscope may act as a guidewire for enabling a medical professional to position the body 1110 and the cap 1115 as desired, and the endoscope may include one or more working channels, which may be used for delivery of additional instruments/accessories to the treatment site. In some embodiments, the cap 1115 may be manipulatable via forceps or other accessory inserted into a working channel of the endoscope, by the medical professional from the proximal end (e.g., external to the patient). In some embodiments, the device and/or accessories may be manipulatable through exterior access points by inserting transcutaneously with a laparoscopic approach to the target tissue.

The body 1110 and/or the distal cap 1115 may include an anchoring mechanism 1130 for engaging an inner surface 1120a of the body lumen 1120. The anchoring mechanism 1130 may be disposed around an outer circumferential surface 1135, 1140 of the respective body 1110 and/or distal cap 1115. The anchoring mechanism 1130 may embed to secure and stabilize the body 1110 and/or distal cap 1115 in the inner surface 1120a of the body lumen 1120 but not perforate, e.g., extend beyond the outer surface 1120b, of the body lumen 1120. It is understood that the body 1110 and/or distal cap 1115 may be engageable with a healthy tissue portion in the body lumen 1120, so that all diseased tissue may be positioned in the selected tissue for resection 1125 (such that the positioning of the body 1110 and the distal cap 1115 a distance "d6" apart from each other surround the selected tissue for resection) and removed by the device 1100.

The anchoring mechanism 1130 may be one or more mechanical fasteners including but not limited to clips, clamps, quills, barbs, and the like. In some embodiments, the anchoring mechanism 1130 may be a suture or other device for securing the body 1110 and/or distal cap 1115 to the inner surface 1120a of the body lumen 1120. In some embodiments, the anchoring mechanism 1130 may be quills disposed in a direction so that the body portion 1110 and/or distal cap 1115 may be rotatable about the axis 1102 in a first direction indicated by arrow 1145 to embed, or lock the quills into the inner surface 1120a of the body lumen 1120. If the body 1110 and/or distal cap 1115 needs readjustment, the body 1110 and/or distal cap 1115 may be rotatable about the axis 1102 in a second direction opposite the first direction (arrow 1145) to release the quills from the inner surface 1120a of the body lumen 1120.

When the body 1110 and the distal cap 1115 are positioned in the body lumen 1120 along the axis 1102 and secured to the inner surface 1120a of the body lumen 1120, the selected tissue for resection 1125 may be drawn inward to the body 1110 by suction, in addition to and/or supplemented by mechanical grasping methods as described above with respect to FIGS. 2, 8F, 9A-9B, and 10A-10E. In some embodiments, a grasping tool may grasp the inner surface 1120a of the selected tissue for resection 1125 and draw the tissue radially inward from the body lumen 1120, as shown at step 1105b in FIG. 11B. For example, as described above, in some embodiments a grasping tool may be delivered to a treatment site through a working channel of an endoscope. The endoscope may allow for articulation of the grasping tool in the distance "d6" between the distal cap 1115 and the body 1110. A medical professional may articulate the grasping tool for grasping selected tissue and drawing the tool inward into the body 1110.

In some embodiments, one or more fasteners such as hooks, barbs, and the like may be disposed on an inner circumferential surface 1150 for securing the selected tissue for resection 1125 (see FIG. 11C). In some embodiments, a suction device as a tissue capture device may be engageable with the body 1110 and initiated to draw the selected tissue for resection 1125 radially inward into the body 1110. For example, suction may be applied to draw the selected tissue for resection 1125 in a proximal direction along the axis 1102 as indicated by arrow 1155.

In some embodiments, an expandable ring 1305 (see FIGS. 13A-13B) may be deployable to the selected tissue for resection 1125. The ring 1305 may be attachable to an inner surface 1120a of the tissue, e.g., by hooks, rings, or other mechanical fasteners. The ring 1305 may have a variable diameter, e.g., be formed of a flexible material, so that the ring 1305 may be collapsible and expandable. The ring 1305 may be attached to the selected tissue for removal (see FIG. 13B), and may be drawn into the body 1110. In some embodiments, a grasping tool 1310 may be used, e.g., having a proximal end outside of the patient for articulation by a medical professional, to draw the selected tissue inward. The grasping tool 1310 may be extendable along the axis 1102, and be pulled in a proximal direction so that the ring may decrease radially to be drawn into the body 1110, thereby drawing the selected tissue into the body 1110 (see FIG. 13B).

In some embodiments, one or more balloons may be utilized to draw the selected tissue for resection 1125 into the body 1110. Referring now to FIGS. 12A-12C, a balloon 1210 may be expanded in the body lumen 1120 and engaged with the selected tissue for resection 1125. The balloon 1210 may include an anchoring mechanism 1215 for engaging the inner surface 1120a of the body lumen at the selected tissue for resection 1125, e.g., by one or more mechanical fasteners, clips, clamps, barbs, hooks, and the like. When the balloon 1210 is engaged with the selected tissue for resection 1125, the balloon 1210 may be deflated, or super deflated (e.g., vacuum applied to fully evacuate the balloon), (see FIG. 12B at step 1205b) so the balloon 1210 may have a webbing effect. For example, as shown in FIGS. 12B-12C, the balloon in a deflated state, indicated by reference numeral 1210' and still engaged with the inner surface 1120a of the body lumen at the selected tissue for resection 1125, may then be retracted in proximal direction to draw the tissue into the body 1110.

At step 1105c as shown in FIG. 11C, the distal cap 1115 may be moved in a proximal direction towards the body 1110 to secure the selected tissue for resection 1125 within the body 1110. In some embodiments, the distal cap 1115 and the body 1110 may be coupled together. For example, the distal cap 1115 and the body 1110 may be coupled together by a mechanical fastener 1160 such as clips, rivets (e.g., POP® rivets), snaps and the like. In some embodiments, T-tags, barbs, and/or hooks may couple the distal cap 1115 and the body 1110.

At step 1205c in FIG. 12C, the distal cap 1115 may be moved in a proximal direction towards the body 1110 to secure the selected tissue for resection 1125 within the body 1110. In some embodiments, the tissue may be captured by a mechanical fastener 1225, such as a t-tag for closure within the body 1110 and the cap 1115. The mechanical fastener 1225 may be deliverable through at least one cavity 1235 in the body 1110. In some embodiments, the mechanical fastener 1225 may be deliverable as an accessory by an endoscope, as described above with respect to other accessories such as tissue resecting devices, tissue grasping tools, and the like.

In embodiments, a tissue resecting device may be deployable for resecting the selected tissue for resection 1125 in the body 1110. As described above with respect to FIGS. 6A-6B, 7A-7C, 8H, 9A-9B, and 10A-10E, the tissue resecting device may be a blade extendable from the distal cap 1115, electrocautery device, and/or radially expanding wire and be similarly operable for resecting the selected tissue for resection 1125 from the body lumen 1120. As described above, a tissue resecting device may be deliverable to a treatment site via a working channel of an endoscope.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the subject matter of the claims.

What is claimed is:

1. A device for tissue resection in a body lumen, the device comprising:
    a body extending along an axis;
    a distal cap positioned distally of the body and coupled to a shaft extending along the axis, the body and the distal cap being movable relative to each other;
    a first balloon disposed on the distal cap and a second balloon disposed on the body proximate a selected tissue for resection in the body lumen;
    a tissue capture device deployable from the tissue resection device such that the selected tissue for resection is securable by the tissue capture device; and
    a tissue resecting device for resecting the selected tissue for resection.

2. The tissue resection device according to claim 1, further comprising a tissue closure device.

3. The tissue resection device according to claim 1, wherein the first and second balloons are expandable to engage the body lumen such that the selected tissue for resection is between the first and second balloons.

4. The tissue resection device according to claim 1, wherein the tissue capture device includes one or more posts disposed circumferentially around a surface of the body and extendable from the body in a direction along the axis for securing the selected tissue for resection against the distal cap.

5. The tissue resection device according to claim 2, wherein the tissue closure device is configured to join portions of the body lumen.

6. The tissue resection device according to claim 1, wherein the tissue resecting device includes a blade disposed circumferentially around a surface of the body and extendable from the body in a direction along the axis for resecting the selected tissue for resection.

7. A device for tissue resection in a body lumen, the device comprising:
    a body extending along an axis;
    a distal cap positioned distally of the body and coupled to a shaft extending along the axis, the body and the distal cap being movable relative to each other;
    an anchor capable of engaging the body and the distal cap proximate a selected tissue for resection in the body lumen;
    a tissue capture device deployable from the tissue resection device such that the selected tissue for resection is securable by the tissue capture device; and
    a blade extendable from the distal cap in a direction along the axis for resecting the selected tissue for resection.

8. The tissue resection device according to claim 7, wherein the blade is disposed circumferentially around a surface of the distal cap and extendable from the distal cap in response to the inner shaft being movable relative to the outer shaft.

9. A system for tissue resection in a body lumen, the system comprising:
    a tissue resection device, including:
    a body extending along an axis;
    a distal cap positioned distally of the body and coupled to a shaft extending along the axis, the body and the distal cap being movable relative to each other;
    a first balloon disposed on the distal cap and a second balloon disposed on the body proximate a selected tissue for resection in the body lumen; and a visualization device for visualizing positioning of the tissue resection device in the body lumen relative to the selected tissue for resection.

10. The system according to claim 9, further comprising:
a tissue capture device deployable from the tissue resection device such that the selected tissue for resection is securable by the tissue capture device;
a tissue resecting device for resecting the selected tissue for resection; and
a tissue closure device.

11. The system according to claim 9, wherein the first and second balloons are expandable to engage the body lumen such that the selected tissue for resection is between the first and second balloons.

12. The system according to claim 9, further comprising a tissue capture device including one or more posts disposed circumferentially around a surface of the body and extendable from the body in a direction along the axis for securing the selected tissue for resection against the distal cap.

13. The system according to claim 10, wherein the tissue resecting device includes a blade disposed circumferentially around a surface of the body and extendable from the body in a direction along the axis for resecting the selected tissue for resection.

14. A system for tissue resection in a body lumen, the system comprising:
a tissue resection device, including:
a body extending along an axis;
a distal cap positioned distally of the body and coupled to a shaft extending along the axis, the body and the distal cap being movable relative to each other; and
an anchor capable of engaging the body and the distal cap proximate a selected tissue for resection in the body lumen; and
a blade extendable from the distal cap in a direction along the axis for resecting the selected tissue for resection; and
a visualization device for visualizing positioning of the tissue resection device in the body lumen relative to the selected tissue for resection.

15. The system according to claim 14, wherein the blade is disposed circumferentially around a surface of the distal cap and extendable from the distal cap in response to the inner shaft being movable relative to the outer shaft.

* * * * *